United States Patent [19]
Bradbury et al.

[11] Patent Number: 5,091,425
[45] Date of Patent: Feb. 25, 1992

[54] 5-(HETEROCYCLYLALKANOYL)AMINO-4-HYDROXYPENTANAMIDES

[75] Inventors: Robert H. Bradbury, Wilmslow; David Brown, Bridge; David A. Roberts, Congleton; David Waterson, Bollington, all of England

[73] Assignee: Imperial Chemical Industries plc, London, England

[21] Appl. No.: 435,687

[22] Filed: Nov. 14, 1989

[30] Foreign Application Priority Data

Nov. 17, 1988 [GB] United Kingdom ............... 8826930
May 25, 1989 [GB] United Kingdom ............... 8912080

[51] Int. Cl.$^5$ ............... C07D 487/04; C07D 263/06; C07D 263/04; A61K 31/495
[52] U.S. Cl. ............... 514/228.5; 514/233.2; 514/249; 544/61; 544/118; 544/336; 544/350; 548/215; 549/321
[58] Field of Search ............... 544/350, 118, 61; 514/222, 232, 234, 249

[56] References Cited

U.S. PATENT DOCUMENTS 4,758,584  7/1988  Bühlmayer et al. ............... 514/18

FOREIGN PATENT DOCUMENTS 0258183  3/1988  European Pat. Off. .
0270234  6/1988  European Pat. Off. .

Primary Examiner—Mark L. Berch
Attorney, Agent, or Firm—Cushman, Darby & Cushman

[57] ABSTRACT

This invention concerns novel nitrogen derivatives of the formula I

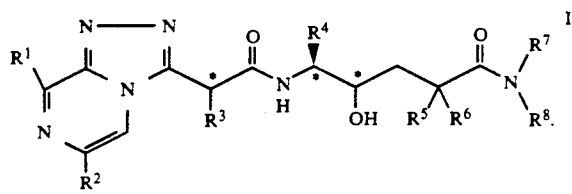

(and their pharmaceutically-acceptable salts), together with pharmaceutical compositions containing them. The nitrogen derivatives are inhibitors of the catalytic action of renin. The invention further concerns novel processes for the manufacture of said inhibitors.

12 Claims, No Drawings

5-(HETEROCYCLYLALKANOYL)AMINO-4-HYDROXYPENTANAMIDES

This invention contains novel heterocyclic amides and, more particularly, it concerns novel 5-(heterocyclylalkanoyl)amino-4-hydroxypentanamides which are inhibitors of the catalytic action of renin, pharmaceutical compositions containing said amides and processes for their manufacture.

Renin is a proteolytic enzyme component of the renin-angiotensinaldosterone cascade system which is closely involved, inter alia, with the maintenance of normal blood pressure in warm-blooded animals such as man. Renin is produced and stored in the juxtaglomerular apparatus of the kidney and may be released into the blood circulation in response to various physiological stimuli such as a decrease in the pressure of the blood entering or within the kidney, a fall in total body blood volume or a reduction in renal distal tubular sodium ion concentration. Once released into the circulation, renin acts on its specific natural substrate, the circulating protein angiotensinogen, to liberate the decapeptide, angiotensin I, which is subsequently cleaved by angiotensin converting enzyme (ACE) to the potent vasoconstrictor and aldosterone releasing peptide, angiotensin II. The latter is further cleaved by an aminopeptidase to give a further pressor substance, angiotensin III, which has potent aldosterone releasing properties on the adrenal cortex and is a moderate vasoconstrictor. Aldosterone itself promotes retention of sodium ions and fluid retention. Accordingly, the release of renin into the circulation tends to produce a hypertensive effect. Inhibitors of the action of renin have therefore been sought for use in the general control of hypertension and congestive heart failure as well as agents for use in the diagnosis of hypertension due to excessive renin levels. The specificity of renin for its substrate angiotensinogen provides a pharmacologically specific means of modifying the renin-angiotensin-aldosterone system.

It has now been discovered that the novel heterocyclic amides of formula I below have surprisingly good inhibitory effects on the action of renin, of value in treating diseases and medical conditions where amelioration of the vasoconstrictor and fluid retaining properties of he renin-angiotensin-aldosterone system is desirable, for example, in treating hypertension, congestive heart failure and/or hyperaldosteronism in warm-blooded animals including man.

According to the invention there is provided a heterocyclic amide of the formula I (set out hereinafter) wherein:

$R^1$ is (1-8C)alkyl or phenyl;

$R^2$ is phenyl or pyridyl, the latter optionally bearing a (1-4C)alkyl substituent;

$R^3$ is hydrogen or a group of the formula $Q^1.A^1$—in which $Q^1$ is selected from pyridyl, imidazolyl, thiazolyl and pyrazolyl, and $A^1$ is methylene or ethylene;

$R^4$ is (1-8C)alkyl or (3-8C)cycloalkyl-(1-4C)alkyl;

$R^5$ is hydrogen or (1-4C)alkyl;

$R^6$ is hydrogen, (1-6C)alkyl, (1-4C)alkoxy, hydroxy, (1-4C)alkylthio, (1-4C)alkylsulphinyl, (1-4C)alkylsulphonyl, or a group of the formula $Q^2.A^2$—in which $Q^2$ is selected from (1-4C)alkoxy, (2-4C)alkenyl, phenyl and hydroxy, and $A^2$ is (1-4C)alkylene; or $R^5$ and $R^6$ together form (2-4C)alkylene;

and wherein $R^7$ is hydrogen, (1-4C)alkyl or hydroxy(2-4C)alkyl; and $R^8$ is hydrogen, (1-4C)alkyl in which 2 or 3 carbon atoms may bear a hydroxy substituent, (1-8C)alkyl, a group of the formula $Q^3.A^3$—in which $Q^3$ is selected from (1-4C)alkoxy, morpholino, thiomorpholino, piperidino, pyrrolidino, N-(1-4Cpiperazinyl, pyridyl (itself optionally bearing a (1-4C)alkyl substituent) and phenyl (itself optionally bearing 1 or 2 substituents independently selected from halogeno, trifluoromethyl, cyano, (1-4C)alkyl, (1-4C)alkoxy, amino(1-4C)alkyl), and $A^3$ is (1-4C)alkylene; or $R^8$ is a group of the formula $Q^4.A^4$—in which $Q^4$ is selected from amino, hydroxy and N,N-di(1-4C)-alkylamino, and $A^4$ is (1-8C)alkylene; or $R^7$ and $R^8$ together with the adjacent nitrogen complete a morpholino, thiomorpholino, piperidino, pyrrolidino or N-(1-4C)piperazinyl moiety; and wherein a phenyl moiety of $R^1$, $R^2$ or $Q^2$, may optionally bear 1 or 2 substituents independently selected from halogeno, trifluoromethyl, cyano, (1-4C)alkyl and (1-4C)alkoxy; or a pharmaceutically acceptable salt thereof when $R^2$, $R^3$, or $R^8$, or $R^7$ and $R^8$ contain a basic group.

The chemical structures referred to herein by Roman numerals are set out together at the end of the specification. The generic term "(1-8C)alkyl" in this specification means an alkyl group of 1 to 8 carbon atoms and includes both straight chain and branched alkyl groups of 3 to 8 carbon atoms. Other generic terms such as "alkylene" are to be interpreted similarly. However, the term "butyl" means the "n-butyl" group, with isomeric groups such as t-butyl, sec- butyl and i-butyl being referred to specifically as necessary. Other specific terms such as "propyl" are to be interpreted similarly. It will be appreciated that the compounds of formula I possess at least 3 chiral centres (shown with an asterisk *) and may therefore exist in racemic or optically active form, or other stereoisomeric mixtures thereof. This invention includes any optical isomer or racemate of formula I, or any other stereoisomeric mixture thereof, which inhibits renin, it being well known in the art how to prepare optical isomers, for example by resolution of the racemic form or by synthesis from optically active starting materials, how to separate stereoisomeric mixtures and how to show their renin inhibitory activity, for example using the standard tests referred to hereinafter. In general, it is preferred that the chiral centres in the fragment of the structure—$CO.NH.CH(R^4).CH(OH).CH_2$- in formula I have the S-configuration.

A particular value for $R^1$, $R^4$ or $R^8$ when it is (1-8C)alkyl is, for example, (1-6C)alkyl, such as methyl, ethyl, propyl, isopropyl, butyl, isobutyl, sec-butyl, t-butyl, pentyl, isopentyl, 1-methylbutyl, hexyl, 1-methylpentyl or 1,1-dimethylbutyl.

A particular value for $R^4$ when it is (3-8C)cycloalkyl(1-4)alkyl is, for example, (3-8C)cycloalkylmethyl such as cyclopropylmethyl, cyclopentylmethyl or cyclohexylmethyl.

A particular value for $R^2$ when it is pyridyl is, for example, 3-pyridyl) and a particular value for an optional (1-4C)alkyl substituent is, for example, methyl or ethyl.

A particular value for $R^5$ or $R^7$ when it is (1-4C)alkyl is, for example, methyl, ethyl, isopropyl or isobutyl.

A particular value for $A^2$ or $A^3$ is, for example, methylene, ethylene, ethylidene or trimethylene, of which values methylene is generally preferred.

A particular value for $R^6$ when it is (1-6C)alkyl is, for example, (1-4C)alkyl such as methyl, ethyl, isopropyl or isobutyl.

A particular value for $R^6$ when it is (1-4C)alkoxy is, for example, methoxy, ethoxy or propoxy.

A particular value for $R^6$ when it is (1-4C)alkylthio is for example, methylthio or ethylthio; when it is (1-4C)alkylsulphinyl is, for example, methylsulphinyl or ethylsulphinyl; and when it is (1-4C)alkylsulphonyl is, for example, methylsulphonyl or ethylsulphonyl.

A particular value for $Q^2$ or $Q^3$ when it is (1-4C)alkoxy is, for example, methoxy, ethoxy, isopropoxy or isobutoxy; and when it is (3-8C)cycloalkyl is, for example, cyclopropyl, cyclobutyl, cyclopentyl or cyclohexyl.

A particular value for $Q^2$ when it is (2-4C)alkenyl is, for example, vinyl, 1-propenyl, allyl or 1-butenyl.

A particular value for $R^5$ and $R^6$ when together they form (2-4C)alkylene is, for example, ethylene, propylene or tetramethylene.

A particular value for $R^7$ when it is hydroxy(2-4C)alkyl is, for example, 2-hydroxyethyl or 2-hydroxypropyl.

A particular value for $R^8$ when it is (2-4C)alkyl in which 2 or 3 carbon atoms bear a hydroxy substituent is, for example, 2-hydroxy-(hydroxymethyl)ethyl or 2-hydroxy-1,1-di(hydroxymethyl)ethyl.

A particular value for $Q^3$ when it is N-(1-4C)alkylpiperazinyl, or for $R^7$ and $R^8$ when together with the adjacent nitrogen they complete a N-(1-4C)alkylpiperazinyl moiety, is, for example, N-methyl-, N-ethyl or N-propylpiperazinyl.

A particular value for a (1-4C)alkyl substituent which may be present when $Q^3$ is pyridyl is, for example, methyl or ethyl.

Particular values for optional substituents which may be present as defined above on phenyl include, for example: for halogeno: fluoro, chloro and bromo; for (1-4C)alkyl: methyl, ethyl, isopropyl and butyl; and for (1-4C)alkoxy: methoxy, ethoxy, propoxy and isopropoxy.

Particular values for optional amino(1-4C)alkyl substituents which may be present when $Q^3$ is phenyl in addition include, for example, aminomethyl, 2-aminoethyl and 3-aminopropyl.

A particular value for $Q^4$ when it is N,N-di[(1-4C)alkyl]amino is, for example, dimethylamino or diethylamino.

A particular value for $A^4$ is, for example, methylene, ethylene, trimethylene or tetramethylene, is any of which an individual methylene may optionally bear a methyl, ethyl, isopropyl or isobutyl substituent.

Specific combinations of values for $R^7$ and $R^8$ include, for example:

(1), when $R^8$ is methyl, ethyl, propyl, butyl, 2-hydroxy-1-(hydroxymethyl)ethyl, 2-hydroxy-1,1-di(hydroxymethyl)ethyl, methoxyethyl, ethoxyethyl, 2-(morpholino)ethyl, 2-pyridylmethyl, 2-(3-pyridyl)ethyl, benzyl, chlorobenzyl, bromobenzyl, cyanobenzyl, 1-phenylethyl, 2-phenylethyl, 2-(hydroxymethyl)-3-methylbutyl, 2-(aminomethyl)-3-methylbutyl, or 2-hydroxy-1,1-dimethylethyl; and $R^7$ is hydrogen, methyl, ethyl or 2-hydroxyethyl; and (2), when $R^7$ and $R^8$ together with he adjacent nitrogen complete a morpholino, piperidino, pyrrolidino or N-methylpiperazino moiety.

A particular group of compounds of the invention of special interest comprise, for example those heterocyclic amides of the formula II wherein $R^{11}$ is (1-6C)alkyl; and $R^2$, $R^5$, $R^6$, $R^7$ and $R^8$ have any of the meanings defined above; together with the pharmaceutically acceptable salts thereof.

A preferred value for $R^1$ or $R^{11}$ is, for example, propyl or isobutyl.

A preferred value for $R^2$ is, for example, 3-pyridyl.

A preferred value for $R^3$ is, for example, hydrogen or pyridylmethyl (especially 3-pyridylmethyl).

A preferred value for $R^4$ is, for example, cyclohexylmethyl.

A preferred value for $R^5$ is, for example, hydrogen or methyl and for $R^6$ is methyl or isopropyl.

Suitable pharmaceutically acceptable salts of heterocyclic amides of formula I which contain a basic group include, for example, salts with inorganic acids such as with hydrogen halides (especially hydrochloride or hydrobromide salts), or with sulphuric or phosphoric acids, and salts with organic acids affording physiologically acceptable anions, for example, salts with acetic, citric, gluconic, tartaric, p-toluenesulphonic or trifluoroacetic acids.

Particular compounds of the invention are described in the accompanying Examples, which compounds are provided together with their appropriate pharmaceutically acceptable salts, as a further feature of the invention. A compound of particular interest is described hereinafter in Example 6.

The heterocyclic amides of formula I may be made by analogy with any process known in the art for the production of structurally related compounds, for example by analogy with the many different procedures known in standard text-books for the formation of amide bonds. Such processes for the production of heterocyclic amides of formula I and pharmaceutically acceptable salts thereof are provided as a further feature of the invention and are illustrated by the following preferred procedures in which $R^1$-$R^8$, $Q^1$-$Q^4$, and $A^1$-$A^4$ have any of the meanings stated above:

a) A carboxylic acid of the formula III, in free acid form or as its alkali metal salt, or a reactive derivative thereof, is reacted with the appropriate amine of the formula IV.

When a free acid of formula III is used, the process is preferably carried out in the presence of a suitable condensing agent, for example, a carbodiimide such as 1,3-dicyclohexylcarbodiimide, 1,3-diisopropylcarbodiimide or 1-ethyl-3-(3-dimethylaminopropyl)-carbodiimide optionally together with an N-hydroxytriazole such as 1-hydroxybenzotriazole and in a suitable solvent or diluent, for example, methylene chloride or dimethylformamide, and at a temperature in the range, for example, $-20°$ to $-35°$ C. and, preferably, at or near ambient temperature. When 1-ethyl-3-(3-dimethylaminopropyl)carbodiimide is used as condensing agent, it is conveniently used in the form of a hydrohalide (such as the hydrochloride) salt and, preferably, in the presence of a suitable organic base, for example, triethylamine. When an alkali metal salt, for example, the sodium salt, of an acid of formula III is used, a condensing agent such as a carbodiimide optionally together with an N-hydroxytriazole is used as described above. However, in this case, when a 1-ethyl-3-(3-dimethylaminopropyl)carbodiimide hydrohalide is used as the condensing agent, no added organic base is required.

A particularly suitable reactive derivative of an acid of formula III is, for example, the acid halide of the said acid, for example the acid chloride (obtainable, for example, by reaction of the acid with a chlorinating agent such as thionyl chloride), a mixed anhydride of the said acid with a (1-4C)alkanoic acid (such as formic acid) or a hemi(1-4C)alkyl carbonater [obtainable, for example, by reaction with an appropriate alkanoyl halide, a (1-45C)alkyl formate or a (1-4C)alkyl chloroformate (such as isobutyl chloroformate)], or an azide of the said acid, (obtainable, for example, by reaction of the acid with diphenylphosphoryl azide and triethylamine or from the corresponding hydrazide of the said acid by reaction with an alkyl nitrite such as t-butyl or amyl nitrite in the presence of strong acid.)

When a reactive derivative of an acid of the formula III is used in process (a), a base such as triethylamine, N-methylmorpholine, N-methylpiperidine or 4-(dimethylamino)pyridine is conveniently also present and the reaction is carried out in a suitable solvent or diluent such as dioxan, N,N-dimethylformamide or methylene chloride and a temperature in the range, for example −40° to 35° C.

The starting materials of formula III and IV may be made by standard procedures of organic chemistry already known for the production of structurally similar compounds and as illustrated in the accompanying Examples. For example, the acids of formula III may be obtained by the procedures shown in Scheme 1. Similarly, the amine derivatives of formula IV may be obtained, for example, by the procedures shown in Scheme 2. It will be appreciated that certain of the reaction stages and in particular the reaction of the dianion of the formula: $(R^5)(R^6)C^-.CO_2^-$ with the iodomethyloxazoline of the formula V to give the carboxylic acid of the formula VI, may give rise to diastereoisomeric mixtures which require to separated so that the desired stereoisoeric form of the amine of formula IV is obtained. This separation may be carried out, for example, by standard chromatographic procedures already generally known in the art of organic chemistry. The starting amines of the formula: $(R^7)(R^8)NH$ required in Scheme 2 are either commercially available or may be obtained by analogy with well known procedures already known for the production of structurally analogous amines.

b) A lactone of the formula VIII is reacted with an amine of the formula: $(R^7)(R^8)NH$.

The process is conveniently carried out at a temperature in the range, for example, 20° to 100° C. and in the presence of a suitable diluent or solvent, for example, an inert solvent such as N,N-dimethylformamide, tetrahydrofuran or t-butyl methyl ether. Alternatively, where the amine of the formula: $(R^7)(R^8)NH$ is an inexpensive volatile liquid, the amine may itself be used in large excess instead of most or all of he conventional solvent or diluent. Equally, where the amine is relatively unreactive, it may be used in process (b) in the form of its dimethylaluminium complex, formed by reaction of the amine with dimethylaluminium chloride or trimethylaluminium in a suitable inert solvent such as methylene chloride and in the absence of oxygen. The process may then be carried out at a temperature in the range, for example, −70° to 60° C.

It will be appreciated that when $R^8$ itself contains an amino substituent, this must preferably first be protected with a suitable amine protecting group, for example, a t-butoxycarbonyl or benzyloxycarbonyl group, before the reaction with the lactone of the formula VI and then the protecting group subsequently removed. The protection of amino groups and their subsequent deprotection is well known in the organic chemical art for analogous compounds such as peptides.

The starting lactones of formula VIII may be made by standard organic chemical procedures, for example, by condensing an aminoalkyl lactone of the formula VII with a carboxylic acid of formula III, as illustrated in the accompanying Examples and as shown in Scheme 3. The aminoalkyl lactones of formula VII may also be obtained, for example, by reaction of the lithium enolate anion of a lactone of the formula IX in which P is a suitable protecting group, for example, t-butoxycarbonyl or benzyloxycarbonyl with an appropriate electrophile. Thus, for example, the following lactones ($R^5$=hydrogen) may be obtained by such a procedure:

| $R^6$ | Reagents |
|---|---|
| alkenyl | alkenyl halide |
| alkylthio | dialkyl sulphide |
| hydroxymethyl | formaldehyde |
| hydroxyethyl | ethylene oxide |
| alkoxyalkyl | alkoxyalkyl halide |
| phenylalkyl | phenylalkyl halide |
| hydroxy | oxygen, followed by dimethyl sulphide |

The lactones of the formula IX may themselves be made by analogy with published procedures such as that described by Kleinman et alia (J. Org. Chem., 1986, 51, 4828).

Alternatively, the aminoalkyl lactones of formula VII may be obtained by reduction of an azidoalkyl lactone of the formula VIIa, for example, by palladium-on-charcoal catalyst hydrogenation at about one atmosphere pressure and ambient temperature in a suitable solvent or diluent such as ethanol or methanol. The said azidoalkyl lactones may themselves be made by analogy with published procedures such as that described in European Patent Application, Publication No. 0258183.

c) When a heterocyclic amide of formula I which contains a (1-4C)alkylsulphinyl or (1-4C)alkylsulphonyl substituent is required, the corresponding compound of the formula I containing a (1-4C)alkylthio substituent is oxidised.

It will be appreciated that, depending on the nature and amount of oxidising agent used, it is possible to produce either the alkylsulphinyl or alkylsulphonyl compounds of formula I. When only alkylsulphonyl compounds are required, the starting material may be the corresponding alkylsulphinyl compound. Equally, by reduction or increase of the reaction temperature within the general range −10° to 45° C., it is possible to predispose the production of sulphinyl or sulphonyl compounds.

Suitable oxidising agents include any conventional oxidants which are compatible with the presence of other sensitive functional groups, for example, alkali metal persulphates (such as potassium peroxymonosulphate), alkali metal periodates (such as sodium or potassium periodate), alkali metal permanganates (such as potassium permanganate), organic peracids (such as perbenzoic acid) and lead tetraacetate. The solvents suitable for use in the process necessarily depend on the oxidising agent used, but include, for example, methanol, formic acid, acetic acid, dichloromethane and chloroform.

When an alkylsulphonyl compound is required, a convenient oxidising agent is, for example, an alkali metal peroxymonosulphate (such as potassium peroxymonosulphate in methanol at a temperature in the range, for example, −10° to 25° C.) and when an alkylsulphinyl compound is required, a convenient oxidising agent is, for example, an alkali metal periodate (such as potassium periodate in aqueous methanol or acetic acid at 10° to 25° C.).

d) A protected derivative of the formula X wherein $P^1$ and $P^2$ are suitable protecting groups, or one of $P^1$ and $P^2$ is hydrogen and the other is a suitable protecting group, is deprotected.

Particularly suitable values for $P^1$ or $P^2$ include, for example, typical hydroxy and imino protecting groups such as arylmethyl (and typically benzyl), which may be removed in process (d), for example, by palladium-on-charcoal catalysed hydrogenation at about atmospheric pressure and ambient temperature in a suitable solvent or diluent such as ethanol or methanol. Particularly suitable values for the hydroxy protecting group $P^2$ include, for example, carbonate ester radicals, such as t-butoxycarbonyl and benzyloxycarbonyl, which may be removed by conventional procedures, such as hydrolysis, or, in the case of benzyloxycarbonyl, hydrogenation. Alternatively, $P^1$ and $P^2$ may conveniently be consolidated into an alkylidene or benzylidene group completing an oxazoline ring with the neighbouring nitrogen and oxygen atoms. Such a combined protecting group may be removed, for example, by mild acid hydrolysis or by using ammonium formate and palladium-on-charcoal in a suitable solvent or diluent, such as aqueous ethanol.

Whereafter, when a pharmaceutically acceptable salt is required, it may be obtained, for example, by reacting the compound of formula I with the appropriate acid or base affording a physiologically acceptable ion.

Whereafter, when a particular optically active form of a compound of formula I is required, it may be obtained, for example, by resolution of the corresponding racemic form, by using the appropriate optically active forms of the starting materials in any one of the aforesaid processes, or by separation of the diastereoisomers by physical methods well known in the art.

As stated previously, the compounds of formula I inhibit the action of renin and thereby have beneficial pharmacological effects in warm-blooded animals (including man) in diseases and medical conditions where amelioration of he vasoconstrictor and fluid retaining properties of the renin-angiotensinaldosterone system is desirable, as further set out hereinafter.

In particular, the compounds of formula I inhibit the catalytic activity of renin and hence the biosynthesis of substances known as angiotensins in warm-blooded animals (including man) and thereby minimise the pharmacological effects associated with their presence. The angiotensins, and in particular that known as angiotensin II, are potent spasmogens especially in the vasculature and are known to increase vascular resistance and blood pressure. In addition, the angiotensins are known to stimulate the release of aldosterone and hence result in vascular congestion and hypertension via sodium and fluid retention mechanisms.

The compounds of formula I will therefore be useful in the treatment of diseases or medical conditions such as hypertension, congestive heart failure and/or hyperaldosteronism in warm-blooded animals (including man), as well as in other diseases or medical conditions in which the renin-angiotensin-aldosterone system plays a significant causative role.

The inhibition of the catalytic activity of renin, and in particular of human renin, may be assessed in vitro using a routine laboratory procedure involving the incubation of a test compound initially at a concentration of 100 micromolar in a buffered mixture containing appropriate concentrations of partially purified human renin and the natural renin substrate angiotensinogen. The formation of the angiotensin known as angiotensin I (which is assayed by a standard radioimmunoassay using procedures well known in the art) is inhibited by those compounds which inhibit the action of renin and the degree of inhibition is readily determined by comparing the angiotensin I generation rate in the presence of the test compound (at the specified test concentration) with the control rate of angiotensin I generation in the absence of the test compound.

In this standard test procedure, compounds which show at least 30% inhibition are retested at lower concentrations to determine their inhibitory potency. For determination of the $IC_{50}$ (concentration for 50% inhibition of the renin catalysed reaction), concentrations are ordinarily chosen to allow testing over at least four orders of magnitude centred about the predicted approximate $IC_{50}$, which latter is subsequently determined from a plot of percentage inhibition against concentration of the test compound. The above procedure may also be carried out using buffered human plasma in order to assess the effects of the test compound on the action of human plasma renin and involves measuring the inhibition of angiotensin I generated by the action of endogenous plasma renin on plasma-bourne angiotensinogen. In general, compounds of formula I will produce significant inhibition in the above tests at a concentration of 100 micromolar or much less. For example, the compound described in Example 6 hereinafter has an $IC_{50}$ of $2 \times 10^{-10}$ M.

The inhibition of renin may also be assessed in vivo using a routine laboratory procedure involving the stimulation of release of endogenous renin in the common marmoset (*Callithrix jacchus*) by introducing a diet of low sodium content and giving three daily oral doses of the diuretic known as frusemide at 25 mg/kg body weight. A test compound is then administered (orally or parenterally) to marmosets to which an arterial catheter has been implanted under anaesthesia and the change in blood pressure and/or plasma renin activity is determined. The determinations may be carried out in terminally anaesthetised or conscious marmosets. To ensure that the effects seen with the test compound are specific to inhibition of the action of renin, the effect of the test compound on the hypertensive response to injected human renin may be compared with its effect on the hypertensive response to injected angiotensin I in anaesthetised marmosets or in alternative animal preparations adapted for blood pressure measurements. Many of the compounds of formula I generally show specific renin inhibitory properties in the above in vivo test at a dose of 50 mg/kg body weight or much less, without any overt toxic or other untoward pharmacological effects.

The compounds of formula I (or pharmaceutically acceptable salts thereof) will generally be administered for therapeutic or prophylactic purposes to warm-blooded animals (including man) requiring such treatment in the form of a pharmaceutical composition in conjunction with a pharmaceutically acceptable diluent or carrier, as is well known in the pharmaceutical art. Such pharmaceutical compositions are provided as a further feature of the invention and will conveniently be in a form suitable for oral administration (for example, as a tablet, capsule, solution, suspension or emulsion) or parenteral administration (for example, as an injectable aqueous or oily solution, or injectable emulsion). The compounds of formula I may also be advantageously administered for therapeutic or prophylactic purposes together with one or more other pharmacological agents known in the general art to be of value in treating one or more of the diseases or medical conditions referred to hereinabove, for example, together with another anti-hypertensive agent such as a diuretic, an adrenergic blocking agent and/or a calcium channel blocking agent.

A compound of formula I will generally be administered to man so that, for example, a daily oral dose of up to 50 mg/kg body weight (and preferably of up to 5 mg/kg) or a daily parenteral dose of up to 10 mg/kg body weight (and preferably of up to 1 mg/kg) is received, given in divided doses as necessary, the precise amount of compound (or pharmaceutically acceptable salt) received and the route and form of administration depending on size, age and sex of the person being treated and on the particular disease or medical condition being treated according to principles well known in the medical arts.

The invention will now be illustrated by the following non-limiting Examples in which, unless otherwise stated:

(i) all evaporations were carried out by rotary evaporation under reduced pressure (0.1-50 mm Hg);

(ii) all operations were carried out at room temperature, that is in the general range 18°-26° C.;

(iii) purification by flash chromatography was performed on silica (Merck Kieselgel: Art.9385) using the procedure described in *J. Org. Chem.*, 1978, 43, 2923, following the purification by thin layer chromatography on silica (0.25 mm, Merck Kieselgel 60F 254 plates: Art. 5715; materials available from E Merck, Darmstadt, Federal Republic of Germany);

(iv) the purity and chemical composition of products was assessed by nuclear magnetic resonance (NMR) spectroscopy, thin layer chromatographic analysis, mass spectroscopy and/or microanalysis;

(v) NMR spectra were determined at 200 MHz using tetramethyl silane (TMS) as an internal standard and are given as chemical shifts in parts per million relative to TMS, using conventional abbreviations for signals, such as: s, singlet; d, doublet; dd, doublet of doublets; t, triplet; m, multiplet; br, broad; and (vi) yields are given for illustration purposes only and are not necessarily the maximum attainable following diligent process development.

EXAMPLE 1

1-Ethyl-3-(3-dimethylaminopropyl)carbodiimide hydrochloride (EDAC) (17.3 mg) was added to a solution of 2-isobutyl-6-phenyl-1,2,4-triazolo[4,3-a]pyrazin-3-ylacetic acid (A) (28 mg), (2S,4S,5S)-5-amino-N-butyl-6-cyclohexyl-4-hydroxy-2-isopropylhexanamide (B) (29 mg), 1-hydroxybenzotriazole hydrate (HOBT) (12.1 mg) and triethylamine (9.1 mg) in N,N-dimethylformamide (DMF) (1 ml). The mixture was allowed to stand overnight. The volatile material was removed by evaporation and the residue partitioned between chloroform (10 ml) and saturated sodium hydrogen carbonate solution (10 ml). The organic phase was separated and washed with water (10 ml), followed by saturated sodium chloride solution (10 ml). The organic phase was dried (MgSO$_4$) and the solvent was removed by evaporation. The residue was purified by flash chromatography, eluting with methanol/ dichloromethane (1:19 v/v), to give (2S,4S,5S)-N-butyl-6-cyclohexyl-4-hydroxy-5-(8-isobutyl-6-phenyl-1,2,4-triazolo[4,3-a]pyrazin-3-yl)-acetamido-2-isopropylhexanamide, as a foam (15 mg); NMR (CDCl$_3$) : 0.5-2.2 (complex m, 36H), 2.6 (m, 1H), 3.1-3.5 (complex m, 4H), 3.7 (m, 1H), 3.9-4.4 (complex m, 3H), 6.9 (br s, 1H), 7.2 (br d, 1H), 7.5 (m, 3H), 8.0 (m, 2H), 8.6 (s, 1H); mass spectrum (positive fast atom bombardment [+veFAB], dimethylsulphoxide (DMSO)/m-nitrobenzyl alcohol): 641 (M+Na)+, 619 (M+H)+, 601, 546, 310, 293.

The starting material (A) was obtained as follows:

(a) A solution of dicyclohexylcarbodiimide (DCC) (157 g) in dichloromethane (200 ml) was added dropwise over 2 hours to an efficiently stirred mixture of powdered sodium 4-methyl-2-oxopentanoate (115.5 g), 2-aminoacetophenone hydrochloride (130.4 g) and HOBT (103 g) in dichloromethane (1 liter). The mixture was stirred overnight and the insoluble dicyclohexylurea removed by filtration. The filtrate was concentrated and the residue redissolved in dichloromethane (500 ml). The mixture was filtered to remove a further quantity of dicyclohexylurea, and the filtrate was washed with saturated sodium hydrogen carbonate solution (500 ml), water (500 ml) and saturated sodium chloride solution (500 ml). The organic phase was dried and concentrated to give 4-methyl-2-oxo-N-(2-oxo-2-phenylethyl)pentanamide (C), as a foam (183.6 g), which was used without further purification; NMR (CDCl$_3$) : 1.0 (d, 6H), 2.2 (m, 1H), 2.8 (d, 2H), 4.75 (d, 2H), 7.4-7.7 (m, 3H), 7.9 (br, 1H), 8.0 (m, 2H).

(b) A solution of the amide C (183.6 g) and ammonium acetate (229.2 g) in ethanol (1200 ml) was heated at reflux for 3.5 hours. The solution was then allowed to stand overnight. The resultant precipitate was filtered to give 3-isobutyl-5-phenylpyrazin-2-ol (D), as pale yellow needles (115.8 g), m.p. 205°-207° C.; NMR (90 MHz, CDCl$_3$): 1.1 (d, 6H), 2.45 (m, 1H), 2.8 (d, 2H), 7.4 (m, 3H), 7.6 (s,1H), 7.8 (m, 2H).

(c) A solution of phosgene in toluene (20% w/v; 220 ml) was added to a solution of D (39.7 g) in tetrahydrofuran (THF) (200 ml) and the solution was heated under reflux for 4 hours. Volatile material was removed by evaporation and the residue was dissolved in ether (500 ml). The solution was washed with saturated sodium hydrogen carbonate solution (500 ml), water (500 ml), and saturated sodium chloride solution (500 ml). The organic phase was dried (MgSO$_4$) and the solvent was removed by evaporation to give 2-chloro-3-isobutyl-5-phenylpyrazine (E), as a brown oil (44 g), which was used without further purification; NMR (90 MHz, CDCl$_3$): 1.0 (d, 6H), 2.3 (m, 1H), 2.85 (d, 2H), 7.4 (m,3H), 7.9 (m, 2H).

(d) A solution of the chloropyrazine E (22 g) and hydrazine hydrate (36 ml) in dimethyl sulphoxide (DMSO) (150 ml) was heated under reflux under an atmosphere of argon for 2 hours. The solution was poured on to an ice-water mixture (500 ml) and the precipitated solid was collected by filtration. The solid was washed well with water and dried under a high vacuum to give 3-isobutyl-5-phenylpyrazin-2-ylhydrazine (F), as an off-white solid (18.8 g), m.p. 109°-110° C. (recrystallized from methanol); NMR (d$_6$-DMSO): 1.0 (d, 6H), 2.3 (m, 1H), 2.65 (d, 2H), 7.4 (m, 3H), 8.0 (m, 2H), 8.6 (s, 1H).

(e) A solution of F (66.4 g) in ethyl acetate (500 ml) was dried (MgSO$_4$). The drying agent was removed by filtration and washed with a further portion of ethyl acetate (200 ml). The combined filtrate and washings were cooled to 0° C. Ethyl malonyl chloride (40.6 g) was then added dropwise to the stirred mixture over 10 minutes. After further stirring at 0° C. for 1 hour, the precipitated solid was collected by filtration, washed with ethyl acetate (200 ml) and suspended in chloroform (500 ml). A solution of sodium hydrogen carbonate (45.3 g) in water (500 ml) was added to the stirred suspension. The organic layer was separated, washed with water (500 ml), followed by saturated sodium chloride solution (500 ml), and dried (MgSO$_4$). The solvent was removed by evaporation to give an oil, which was triturated with ether/hexane (1:1 v/v; 500 ml) to give ethyl [2-(3-isobutyl-5-phenylpyrazin-2-yl)hydrazino]carbonylacetate (G), as a white solid (54 g), m.p. 116°–118° C.; NMR (CDCl$_3$): 1.0 (d, 6H), 1.3 (t, 3H), 2.4 (m, 1H), 2.7 (d, 2H), 3.5 (s, 2H), 4.3 (q, 2H), 7.2 (br, 1H), 7.4 (m, 3H), 7.9 (m, 2H), 8.4 (s, 1H), 9.7 (br, 1H).

(f) A solution of G (53 g) and p-toluenesulphonic acid monohydrate (2.8 g) in toluene (500 ml) was heated under reflux for 2.5 hours. The solvent was removed by evaporation and the residue was dissolved in chloroform (300 ml). The solution was washed with saturated sodium hydrogen carbonate solution (300 ml, water (300 ml) and saturated sodium chloride solution (300 ml). The solution was dried (MgSO$_4$) and the solvent was removed by evaporation. The residue was triturated with ether/hexane (1:1 v/v; 300 ml) to give ethyl 8-isobutyl-6-phenyl-1,2,4-triazolo[4,3-a]pyrazin-3-ylacetate (H), as a white solid (37.1 g), m.p. 105°–107° C.; NMR (90 MHz, CDCl$_3$): 1.0 (d, 6H), 1.2 (t, 3H), 2.6 (m, 1H), 3.2 (d, 2H), 4.2 (q, 2H), 4.3 (s, 2H), 7.4 (m, 3H), 7.9 (m, 2H), 8.1 (s, 1H).

(g) 2M Aqueous sodium hydroxide solution (15 ml) was added to a solution of the ester H (4.5 g) in ethanol (75 ml). The mixture was stirred for 1 hour and then volatile material was removed by evaporation. The residue was dissolved in water (250 ml). The solution was washed with ethyl acetate (50 ml), cooled to 0° C. and acidified to pH 3 with 1 M hydrochloric acid. The precipitated solid was collected by filtration and dried under a high vacuum to give 8-isobutyl-6-phenyl-1,2,4-triazolo[4,3-a]pyrazin-3-ylacetic acid (A), as a white solid (3.9 g), m.p. 160° C. (re-solidifies and re-melts at 181°–183° C.) (from methanol; NMR (d$_6$-DMSO): 1.0 (d, 6H), 2.5 (m, 1H), 3.15 (d, 2H), 4.4 (s, 2H), 7.5 (m, 3H), 8.1 (m, 2H), 9.0 (s, 1H).

The starting material B was obtained as follows:

(h) A 1.6 M solution of butyllithium in hexane (7.8 ml) was added to a stirred solution of diisopropylamine (1.26 g) in dry THF (10 ml) at 0° C. under an atmosphere of argon. The temperature was maintained at 0° C. for 30 minutes, and then a solution of iso-valeric acid (0.63 g) in dry THF (5 ml) was added. The solution was heated at 35° C. for 30 minutes and then cooled to ambient temperature. Hexamethylphosphoramide (HMPA) (1.11 g) was added followed by a solution of (5R,4S)-3-benzyloxycarbonyl-4-cyclohexylmethyl-5-iodomethyl-2,2-dimethyl-1,3-oxazolidine (obtained as described in J.Med.Chem., 1988, 31, 1839) (589 mg) in dry THF (5 ml). The solution was stirred for 2 hours and was then added to saturated ammonium chloride solution (50 ml). The mixture was extracted with ethyl acetate (3×30 ml). The combined extracts were washed with water (30 ml), saturated sodium chloride solution (30 ml) and dried (MgSO$_4$). The solvent was removed by evaporation to give crude (2RS)-2-[(4S,5S)-3-benzyloxycarbonyl-4-cyclohexylmethyl-2,2-dimethyl-1,3-oxazolidin-5-yl]methyl-3-methylbutanoic acid (I), as a clear oil (551 mg), which was used without further purification. For the purposes of characterisation a sample was purified by flash chromatography eluting with ethyl acetate/hexane (1:4 v/v); NMR (CDCl$_3$): 0.8–2.1 (complex m, 28H), 2.3, 2.6 (both m, integration ratio 1:1, total 1H). 3.75 (m, 1H). 3.9 (m, 1H), 5.1 (m, 2H), 7.4 (m, 5H).

(i) The crude carboxylic acid (I) (551 mg) was dissolved in DMF (10 ml) containing triethylamine (126 mg). Butylamine (109 mg), HOBT (169 mg) and EDAC (240 mg) were added and the solution was allowed to stand overnight. The solvent was removed by evaporation and the residue partitioned between ethyl acetate (20 ml) and water (20 ml). The organic layer was separated and washed with saturated sodium hydrogen carbonate solution (20 ml), followed by water (20 ml) and then saturated sodium chloride solution (20 ml). The organic phase was dried (MgSO$_4$) and the solvent was removed by evaporation. The residue was purified by flash chromatography eluting with ethyl acetate/hexane (1:4 v/v), to give initially (2S)-2-[(4S,5S)-3-benzyloxycarbonyl-4-cyclohexylmethyl-2,2-dimethyl-1,3-oxazolidin-5-yl]methyl-N-butyl-3-methylbutanamide (J), as a clear oil (103 mg); NMR (CDCl$_3$): 0.9 (m, 9H), 1.0–2.1 (complex m, 27H), 3.25 (q, 2H), 3.75 (m, 2H), 5.1 (dd, 2H), 5.6 (br, 1H), 7.3 (m, 5H); and then the corresponding (2R)-isomer, as a clear oil (133 mg); NMR (CDCl$_3$): 0.9 (m, 9H), 1.0–2.1 (complex m, 27H), 3.25 (m, 2H), 3.75 (m, 1H), 3.9 (m, 1H), 5.1 (dd, 2H), 5.4 (br, 1H), 7.4 (m, 5H).

(j) Ammonium formate (250 mg) was added to a mixture of the amide J (500 mg) and 10% palladium on charcoal catalyst (250 mg) in water/ethanol (1:9 v/v; 25 ml). The mixture was stirred for 2 hours and then the catalyst was removed by filtration through diatomaceous earth and washed with ethanol (25 ml) and water (25 ml). The combined filtrate and washings were allowed to stand for 30 minutes and then volatile material was removed by evaporation. The residue was dissolved in chloroform (50 ml) and the solution was dried (MgSO$_4$). The solvent was removed by evaporation to give (2S,4S,5S)-5-amino-N-butyl-6-cyclohexyl-4-hydroxy-2-isopropylhexanamide (B), as a foam (337 mg); NMR (CDCl$_3$): 0.8–2.3 (complex H, 30H), 2.6 (ddd, 1H), 3.1 (ddd, 1H), 3.3 (m, 2H), 5.85 (br t, 1H).

EXAMPLE 2

Using a similar procedure to that described in Example 1, there was obtained (2R,4S,5S)-N-butyl-6-cyclohexyl-4-hydroxy-5-(8-isobutyl-6-cyclohexyl-4-hydroxy-5-(8-isobutyl-6-phenyl-1,2,4-triazolo[4,3-a]pyrazin-3-yl)acetamido-2-isopropylhexanamide, as a glassy solid, in 16% yield; NMR (d$_6$-DMSO/d$_4$-acetic acid): 0.5–1.8 (complex m, 36H), 2.5 (m, 1H), 3.0–3.2 (complex m, 4H), 3.4 (m, 1H), 4.0 (m, 1H), 4.3 (m, partially exchanged with d$_4$-acetic acid), 7.5 (m, 3H), 8.1 (m, 2H), 8.8 (s, 1H); mass spectrum (+ve FAB, DMSO/m-nitrobenzyl alcohol): 641 (M+Na)$^+$, 619 (M+H)$^+$, 601, 546, 327, 293, 254, 236; microanalysis, found: C, 68.1; H, 8.8; N, 13.0%; C$_{36}$H$_{34}$N$_6$O$_3$.H$_2$O requires: C, 67.9; H, 8.7; N, 13.6%; starting from (2R,4S,5S)-5-amino-N-butyl-6-cyclohexyl-4-hydroxy-2-isopropylhexanamide, itself obtained as a clear oil, in 94% yield; NMR (CDCl$_3$): 0.7–1.9 (complex m, 29H), 2.1 (m, 1H), 3.0 (m, 2H), 3.4 (m, 1H), 3.6 (m, 1H), 6.9 (br, 1H), 8.5 (br, 1H); starting from (2R)-2-[(4S,5S)-3-benzyloxycarbonyl-4-cyclohexylmethyl-2,2-dimethyl-1,3-oxazolidin-5-yl]methyl-N-butyl-3-methylbutanamide, using a similar procedure to that described in Example 1(j).

EXAMPLE 3

EDAC (38 mg) was added to a solution of sodium 2-[8-isobutyl-6-phenyl-1,2,4-triazolo[4,3-a]pyrazin-3-yl]-3-(3-pyridyl)propanoate (A) (86 mg), 2S,4S,5S)-5-amino-N-butyl-6-cyclohexyl-4-hydroxy-2-isopropyl-hexanamide (65 mg) and HOBT (27 mg) in DMF (5 ml). The mixture was allowed to stand overnight, and then worked-up and purified, using a similar procedure to that described in Example 1, to give (2S,4S,5S)-N-butyl-6-cyclohexyl-4-hydroxy-5-(2RS)-[2-(8-isobutyl-6-phenyl-1,2,4-triazolo[4,3-a]pyrazin-3-yl)-3-(3-pyridyl)]-propionamido-2-isopropylhexanamide, as a foam (31 mg); NMR (d$_6$-DMSO/d$_4$-acetic acid): 0.5-2.1 (complex m, 36H), 2.5 (m, 1H), 2.9-3.3 (complex m, 4H), 3.4 (m, 1H), 3.7 (m, 1H), 3.9 (m, 2H), 5.0 (m, 1H), 7.5 (m, 3H), 7.7 (m, 1H), 8.1 (m, 2H), 8.3 (d, 1h), 8.6 (m, 1H), 8.8 (s, 1H), 8.9 (2 singlets, ratio 1:1, 1H); mass spectrum (+ve FAB, methanol/m-nitrobenzyl alcohol): 710 (M+H)+, 637, 401, 384, 356, 314, 293.

The starting material A, was obtained as follows:

(a) Sodium hydride (202 mg) was added to a solution of ethyl 8-isobutyl-6-phenyl-1,2,4-triazolo[4,3-a]pyrazin-3-ylacetate (1.35 g) in DMF (10 ml) with stirring at 0° C. under an atmosphere of argon. When evolution of hydrogen had ceased (approximately 15 minutes), a solution of 3-chloromethylpyridine hydrochloride (722 mg) in DMF (5 ml) was added dropwise over 5 minutes. The mixture was stirred at 0° C. until hydrogen evolution ceased and then at ambient temperature for 2 hours. The mixture was added to ice-cold 0.5 M hydrochloric acid (60 ml). The solution was washed with ether (50 ml) and then basified by addition of solid sodium hydrogen carbonate. The resulting emulsion was extracted with ethyl acetate (2×50 ml). The combined extracts were washed with water (50 ml), followed by saturated sodium chloride solution (50 ml) and dried (MgSO$_4$). The solvent was removed by evaporation and the residue was purified by flash chromatography, eluting with methanol/dichloromethane (3:97 v/v), to give ethyl 2-[8-isobutyl-6-phenyl-1,2,4-triazolo[4,3-a]pyrazin-3-yl]-3-(3-pyridyl)propionate (B), as a white powder (1.1 g), m.p. 110°-111° (after trituration with ether); NMR (CDCl$_3$): 1.1 (d, 6H), 1.2 (t, 3H), 2.6 (m, 1H), 3.3 (d, 2H), 3.75 (ddd, 2H), 4.2 (q, 2H), 4.5 (t, 1H), 7.2 (dd, 1H), 7.5 (m,3H), 7.6 (m, 1H), 7.9 (m, 2H), 7.9 (dd, 1H), 8.2 (s, 1H), 8.4 (dd, 1H), 8.6 (d, 1H).

(b) 0.2 M Aqueous sodium hydroxide solution (6.25 ml) was added to a solution of the ester B (536 mg) in ethanol (20 ml), and the mixture was allowed to stand for 1.5 hours. The volatile material was removed by evaporation and the residue was dissolved in ethanol (20 ml). The volatile material was again removed by evaporation and the residue was dried under high vacuum to give sodium 2-[8-isobutyl-6-phenyl-1,2,4-triazolo[4,3-a]pyrazin-3-yl]-3-(3-pyridyl)propionate (A), as a white powder (529 mg), which was used without further purification; NMR (d$_6$-DMSO) : 1.0 (d, 6H), 2.5 (m, 1H), 3.1 (d, 2H), 3.5 (ddd, 2H), 4.3 (dd, 1H), 7.5 (m, 3H), 7.65 (m, 1H), 8.0 (m, 2H), 8.3 (dd, 1H), 8.5 (d, 1H), 8.9 (s, 1H).

EXAMPLE 4

A solution of sodium 8-propyl-6-(3-pyridyl)-1,2,4-triazolo[4,3-a]pyrazin-3-ylacetate (A) (112 mg) in water (1.5 ml) was added to a solution of (2S,4S,5S)-5-amino-N-butyl-6-cyclohexyl-4-hydroxy-2-isopropylhexana-mide (114 mg) in DMF (13.5 ml). HOBT (47 mg) and EDAC (67 mg) were added, and the solution was allowed to stand overnight. A further quantity of EDAC (67 mg) was added and the solution was again allowed to stand overnight. The reaction mixture was worked up using a similar procedure to that described in Example 1, and purified by flash chromatography eluting with methanol/ dichloromethane (6:94 v/v) to give (2S,4S,5S)-N-butyl-6-cyclohexyl-4-hydroxy-2-isopropyl-5-[8-propyl-6-(3-pyridyl)-1,2,4-triazolo[4,3-a]pyrazin-3-yl]acetamidohexanamide, as a foam (60 mg); NMR (d$_6$-DMSO/d$_4$-acetic acid): 0.8-1.8 (complex m, 32H), 2.1 (m, 3H), 2.8-3.5 (m, 5H0, 3.8 (m, 1H), 4.4 (m, partially exchanged with d$_4$-acetic acid), 7.7 (dd, 1H), 8.6 (m, 1H), 8.7 (d, 1H), 8.9 (s, 1H), 9.3 (s, 1H); mass spectrum (+ve FAB, methanol/glycerol: 606 (M+H)+, 533, 327, 297, 290; microanalysis, found: C, 6.34; H, 8.1; N, 14.8%; C$_{34}$H$_{51}$N$_7$O$_3$,2H$_2$O requires C, 63.7; H, 8.6; N, 15.3%.

The starting material A was obtained as follows:

(a) A solution of DCC (33 g) in dichloromethane (100 ml) was added dropwise over 1 hour to a stirred suspension of powdered sodium 2-oxopentanoate (22. g), 2-oxo-2-(3-pyridyl)ethylamine dihydro-chloride (obtained as described in J. Chem.Soc, 1938, 753) (33.4 g) and HOBT (21.6 g) in dichloromethane (800 ml) containing triethylamine (16.2 g). The reaction mixture was stirred overnight and then worked-up using a similar procedure to that described in Example 1(a) to give 2-oxo-N-[2-oxo-2-(3-pyridyl)]ethylpentanamide (B), as a foam (30.4 g); NMR (90 MHz, d$_6$-DMSO): 0.9 (t, 3H), 1.5 (m, 2H), 2.8 (t, 3H), 4.6 (d, 2H), 7.5 (dd, 1H), 8.2 (dt, 1H), 8.7 (d+brs, 2H), 9.1 (s, 1H).

(b) A solution of the amide B (17.6 g) and ammonium acetate (23.2 g) in ethanol (150 ml) was heated under reflux for 1 hour. The solvent was removed by evaporation and the residue was dissolved in chloroform (200 ml). The solution was washed successively with water (200 ml), saturated sodium hydrogen carbonate solution (200 ml), water (200 ml) and saturated sodium chloride solution (200 ml), and then dried (MgSO$_4$). The solvent was removed by evaporation to give 3-propyl-5-(3-pyridyl)pyrazin-2-ol (C), as an off-white powder (13.4 g), m.p. 193°-195° C. (from ethanol); NMR (90 MHz, d$_6$-DMSO): 1.0 (t, 3H), 1.7 (m, 2H), 2.7 (t, 2H), 7.4 (dd, 1H), 7.95 (s, 1H), 8.2 (dt, 1H), 8.45 (dd, 1H), 9.1 (d, 1H).

(c) A solution of C (7.0 g) in phosphoryl chloride (35 ml) was heated under reflux for 2 hours. Excess phosphoryl chloride was removed by evaporation and the residue was added to an ice-water mixture (200 ml). The temperature of the mixture was maintained at 0° C. and extracted with chloroform (2×100 ml). The combined extracts were washed with water (100 ml), saturated sodium chloride solution (100 ml) and dried (MgSO$_4$). The solvent was removed by evaporation to give 2-chloro-3-propyl-5-(3-pyridyl)pyrazine (D), as a dark oil (5.3 g); NMR (90 MHz, d$_6$-DMSO): 1.0 (t, 3H), 1.8 (m, 2H). 2.9 (t, 2H), 7.5 (dd, 1H0, 8.4 (dt, 1H), 8.65 (dd, 1H), 8.95 (s, 1H), 9.25 (dd, 1H). (d) A solution of the chloropyrazine D (7.2 g) and hydrazine hydrate (29.8 ml) in butanol (150 ml) was heated under reflux for 15 hours, and then allowed to cool. The solid precipitate was collected by filtration and dried under high vacuum to give 3-propyl-5-(3-pyridyl)pyrazin-2-ylhydrazine (E), as an off-white solid (6.1 g), m.p. 164°–165° C. (from methanol); NMR (CDCl$_3$): 1.05 (t, 3H), 1.9 (m, 2H), 2.65 (t, 2H), 7.35 (dd, 1H), 8.25 (dt, 1H), 8.45 (s, 1H), 8.6 (dd, 1H), 9.15 (dd, 1H).

(e) A solution of E (8.8 g) in chloroform (150 ml) was dried over magnesium sulphate. The drying agent was removed by filtration and washed with a further portion of chloroform (50 ml). The two volumes of chloroform were combined, cooled to 0° C. and triethylamine (4.3 g) was added. A solution of ethyl malonyl chloride (7.0 g) in chloroform (50 ml) was added dropwise with stirring over 10 minutes. The mixture was stirred at 0° C. for 1 hour and then at 20° C. for 1 hour. Water (100 ml) was added and the aqueous layer separated and extracted with a further portion of chloroform (100 ml). The combined organic solutions were washed with a solution of sodium acetate (9.5 g) in water (100 ml), water (100 ml) and saturated sodium chloride solution (100 ml), and then dried (MgSO$_4$). The solvent was removed by evaporation to give ethyl [2-[3-propyl-5-(3-pyridyl)pyrazin-2-yl]hydrazino]carbonylacetate (F) as a white solid, m.p. 141°–142° C. (recrystallised from ethyl acetate/hexane); NMR (CDCl$_3$): 1.1 (t, 3H), 1.3 (t, 3H), 1.9 (m, 2H), 2.75 (t, 2H), 3.5 (s, 2H), 4.3 (q, 2H), 7.4 (dd, 1H), 8.25 (dt, 1H), 8.45 (s, 1H), 8.6 (dd, 1H), 9.15 (d, 1H).

(f) A solution of F (8.0 g) and p-toluenesulphonic acid monohydrate (0.45 g) in toluene (200 ml) was heated under reflux for 3 hours. The solvent was removed by evaporation and the residue was partitioned between chloroform (200 ml) and saturated sodium hydrogen carbonate solution (100 ml). The organic layer was separated, washed with water (100 ml) and saturated sodium chloride solution (100 ml), and then dried (MgSO$_4$). The solvent was removed by evaporation to give ethyl 8-propyl-6-(3-pyridyl)-1,2,4-triazolo[4,3-a]pyrazin-3-ylacetate (G), as a white solid (7.7 g), m.p. 130°–131° C. (recrystallised from ethyl acetate/hexane); NMR (CDCl$_3$): 1.1 (t, 3H), 1.3 (t, 3H), 2.1 (m, 2H), 3.4 (t, 2H), 4.25 (q, 2H), 4.35 (s, 2H), 7.45 (dd, 1H), 8.25 (s, 1H), 8.35 (dt, 1H), 8.7 (dd, 1H), 9.2 (d, 1H).

(g) The ester G (112 mg) was hydrolysed with 0.2 M aqueous sodium hydroxide solution (1.75 ml) in ethanol (5 ml) using a similar procedure to that described in Example 3(b) to give sodium 8-propyl-6-(3-pyridyl)-1,2,4-triazolo[4,3a]pyrazin-3-ylacetate (A) as a white solid (110 mg), which was used without further purification or characterisation.

EXAMPLE 5

A solution of N-[2-cyclohexyl-1-(S)-[(3R,5S)-2,3,4,5-tetrahydro-3-isopropyl-2-oxofur-5-yl]ethyl-2-[8-propyl-6-(3-pyridyl)-1,2,4-triazolo[4,3-a]pyrazin-3-yl]acetamide (A) 80 mg) in butylamine (5 ml) was heated under reflux for 4 hours and then the volatile material was removed by evaporation. The residue was purified by flash chromatography, eluting with methanol/dichloromethane (6:94 v/v) to give (2R,4S,5S)-N-butyl-6-cyclohexyl-4-hydroxy-2-isopropyl-5-([8-propyl-6-(3-pyridyl)-1,2,4-triazolo[4,3-a]pyrazin-3-yl]acetamido)-hexanamide, as a foam (60 mg); NMR (d$_6$-DMSO/d$_4$-acetic acid): 0.4–1.8 (complex m, 33H), 1.9 (m, 2H0, 2.95 (m, 2H), 3.15 (t, 2H), 3.3 (m, 1H), 3.9 (m, 1H), 4.3 (m, partially exchanged with d$_4$-acetic acid), 7.5 (dd, 1H), 8.4 (m, 1H), 8.6 (d, 1H), 8.9 (s, 1H), 9.2 (s, 1H); mass spectrum (+ve FAB, DMSO/m-nitrobenzyl alcohol): 606 (M+H$^+$), 533, 327, 297, 290.

The starting material A was obtained as follows:

(a) 2M Hydrochloric acid (5 ml) was added to a solution of crude 2-(RS)-[(4S, 5S)-3-benzyloxycarbonyl-4-cyclohexylmethyl-2,2-dimethyl-1,3-oxazolidin-5-yl]methyl-3-methylbutanoic acid (408 mg) in dioxan (15 ml) and the mixture was allowed to stand overnight. The solvent was removed by evaporation and the residue was partitioned between ethyl acetate (20 ml) and water (20 ml). The organic layer was separated, washed with saturated sodium chloride solution (20 ml) and dried (MgSO$_4$). The solvent was removed by evaporation and the residue was purified by flash chromatography, eluting with ethyl acetate/ hexane (15:85 v/v), to give initially, (3S,5S)-[5-(1S)-(1-benzyloxycarbonylamino-2-cyclohexyl)ethyl-3-isopropyl]tetrahydro-2-furanone, as a solid (49 mg), m.. 159°–161° C. (recrystallised from hexane); NMR (CDCl$_3$): 0.8–1.9 (complex m, 19H), 2.1 (m, 3H), 2.5 (m, 1H), 3.9 (m, 1H), 4.4 (dt, 1H), 4.6 (br d, 1H), 5.1 (s, 2H), 7.35 (m, 5H); and then (3R,5S)-5-[(1S)-(1-benzyloxycarbonylamino-2-cyclohexyl)-ethyl-3-isopropyl]tetrahydro-2-furanone (B), as a solid (110 mg), m.p. 134°–135° C. (recrystallised from hexane); NMR (CDCl$_3$): 0.8–1.9 (complex m, 19H), 2.1 (m, 3H), 2.6 (m, 1H), 3.9 (m, 1H), 4.35 (m, 1H), 4.7 (br d, 1H), 5.1 (dd, 1H), 7.35 (m, 5H).

(b) Ammonium formate (68 mg) was added to B (105 mg) and 10% palladium on charcoal catalyst (52 mg) in ethanol (10 ml). The mixture was stirred for 1 hour and then the catalyst was removed by filtration through diatomaceous earth and washed with ethanol (10 ml). The filtrate and washings were combined and the solvent was removed by evaporation to give (3R,5S)-5-[(1S)-(1-amino-2-cyclohexyl)ethyl-3-isopropyl]tetrahydro-2-furanone (C), as a clear oil (64 mg), which was used without characterisation or purification.

(c) A solution of sodium 8-propyl-6-(3-pyridyl)-1,2,4-triazolo[4,3-a]pyrazin-3-ylacetate (88 mg) in water (1 ml) was added to a solution of C (64 mg) in DMF (9 ml). HOBT (36 mg) and EDAC (104 mg) were added and the solution was allowed to stand overnight. The reaction mixture was worked-up and purified by a similar procedure to that described in Example 1 to give N-((1S)-2-cyclohexyl-1-[(3R,5S)-2,3,4,5-tetrahydro-3-isopropyl-2-oxofur-5-yl]ethyl)-2-[8-propyl-6-(3-pyridyl)-1,2,4-triazolo[4,3-a]pyrazin-3-yl]acetamide (A), as a foam (136 mg); NMR (CDCl$_3$) : 0.7–2.2 (complex m, 27H), 2.6 (ddd, 1H), 3.4 (t, 1H), 4.2–4.45 (m, 4H), 7.5 (dd, 1H), 8.4 (m, 1H), 8.65 (s, 1H), 8.7 (m, 1H), 9.3 (d, 1H).

EXAMPLE 6

A solution of sodium 2-[8-propyl-6-(3-pyridyl)-1,2,4-triazolo[4,3-a]pyrazin-3-yl]-3-(3-pyridyl)propionate (A) (120 mg) in water (1 ml) was added to a solution of (2S,4S,5S)-5-amino-N-butyl-6-cyclohexyl-4-hydroxy-2-isopropylhexanamide (98 mg) in DMF (9 ml). HOBT (40.5 mg) and EDAC (115 mg) were added and the solution was allowed to stand overnight. The reaction mixture was worked up by a similar procedure to that described in Example 1, followed by flash chromatography eluting with methanol/dichloromethane (7:93 v/v) to give (2S,4S,5S)-N-butyl-6-cyclohexyl-4-hydroxy-2-isopropyl-5-[(2RS)-2-(8-propyl-6-(3-pyridyl)-1,2,4-triazolo[4,3-a]pyrazin-3-yl)-3-(3-pyridyl)propionamido]hexanamide, as a foam (77 mg); NMR (d$_6$-DMSO/ D$_4$-acetic acid): 0.2–1.8 (complex m, 33H), 2.0

(m, 2H), 2.9–4.0 (complex m, 8H), 4.9 (m, 1H), 7.4 (m, 1H), 7.5 (m, 1H), 7.9 (m, 1H), 8.5 (m, 2H), 8.7 (m, 2H), 9.3 (m, 2H); mass spectrum (+ve FAB, DMSO/m-nitrobenzyl alcohol): 697 (M+H)$^+$, 624; microanalysis, found: C, 62.1; H, 7.9; N, 16.0%; $C_{41}H_{56}N_8O_3 \cdot 2H_2O$ requires: C, 67.2; H, 8.2; N, 15.3%.

The starting material A was obtained as follows:

(a) Using a similar procedure to that described in Example 3(a), except that the reaction mixture was stirred for 8 hours, instead of 2 hours, at ambient temperature, and the purification by flash chromatography was carried out using methanol/dichloromethane (1:19 v/v gradually increasing to 1:9 v/v) as eluant, there was obtained ethyl 2-[8-propyl-6-(3-pyridyl)-1,2,4-triazolo[4,3-a]pyrazin-3-yl]-3-(3-pyridyl)propionate (B), as an off-white solid, in 47% yield, m.p. 142°–143° C. (after trituration with ether); NMR (CDCl$_3$): 1.1 (d,3H), 1.2 (t, 3H), 2.1 (m, 1H), 3.4 (t, 2H), 3.75 (ddd, 2H), 4.2 (q, 2H), 4.6 (t, 1H), 7.2 (dd, 1H), 7.45 (dd, 1H), 7.6 (dt, 1H), 8.2 (s, 1H), 8.3 (dt, 1H), 8.4 (d, 1H), 8.55 (brs, 1H), 8.7 (1H, dd), 9.1 (1H, d); starting from ethyl 8-propyl-6-(3-pyridyl)-1,2,4-triazolo[4,3-a]-pyrazin-3-ylacetate.

(b) The ester B (125 mg) was hydrolysed with 0.2 M aqueous sodium hydroxide solution (1.5 ml) in ethanol (4.5 ml) using a similar procedure to that described in Example 3 (b) to give sodium 2-[8-propyl-6-(3-pyridyl)-1,2,4-triazo[4,3-a]pyrazin-3-yl]-3-(3-pyridyl)-propionate (A), as an off-white solid (120 mg); NMR (d$_6$-DMSO): 1.0 (t, 3H), 1.95 (m, 2H), 3.3 (t, 3H), 3.4–3.7 (m,2H), 4.3 (dd, 1H), 7.2 (m, 1H), 7.5 (dd, 1H), 7.6 (m, 1H), 8.2–8.5 (m, 3H), 8.6 (dd, 1H), 9.0 (s, 1H), 9.2 (d, 1H).

EXAMPLE 7

A solution of sodium 8-propyl-6-(3-pyridyl)-1,2,4-triazolo[4,3-a]pyrazin-3-ylacetate (128 mg) in water (1.5 ml) was added to a solution of (2S,4S,5S)-5-amino-6-cyclohexyl-4-hydroxy-2-isopropyl-N-methylhexanamide (A) (115 mg) in DMF (13.5 ml). HOBT (54 mg) and EDAC (77 mg) were added and the solution was allowed to stand overnight. The reaction mixture was worked up by a similar procedure to that described in Example 1, followed by flash chromatography eluting with methanol/dichloromethane (1:9 v/v) to give (2S,4S,4S)-6-cyclohexyl-4-hydroxy-2-isopropyl-N-methyl-5-[8-propyl-6-(3-pyridyl)-1,2,4-triazolo[4,3-a]pyrazin-3-yl]acetamidohexanamide, as a foam (65 mg); NMR (d$_6$-DMSO/d$_4$-acetic acid): 0.7 (d, 6H), 0.8–1.7 (complex m, 19H), 2.0 (m, 2H), 2.2 (m, 1H), 2.6 (s, 3H), 3.25 (m and t, 3H), 3.75 (m, 1H), 4.3 (m, partially exchanged with d$_4$-acetic acid), 7.6 (dd, 1H), 8.4 (dt, 1H), 8.6 (d, 1H), 9.0 (s, 1H), 9.3 (dd, 1H); mass spectrum (+ve FAB,DMSO/m-nitrobenzyl alcohol) : 586 (M+Na)$^+$, 564 (M+H)$^+$, 546, 533, 406, 297, 280, 253; microanalysis, found: C, 63.6; H, 7.8; N, 16.6%; $C_{31}H_{45}N_7O_3 \cdot H_2O$ requires : C, 64.0; H, 8.1; N, 16.8%.

The starting material A was obtained as follows:

(a) Methylamine hydrochloride (113 mg) was finely divided and stirred in DMF (10 ml) containing triethylamine (339 mg) until a clear solution was obtained (approximately 1 hour). A solution of crude (2RS)-2-[(4S,5S)-3-benzyloxycarbonyl-4-cyclohexylmethyl-2,2-dimethyl-1,3-oxazolidin-5-yl]methyl-3-methylbutanoic acid (750 mg) in DMF (5 ml) was added, followed by HOBT (227 mg) and EDAC (322 mg), and the reaction mixture was allowed to stand overnight. The reaction mixture was worked-up using a similar procedure to that described in Example 1(i). The residue was purified by flash chromatography eluting with ethyl acetate/hexane (3:7 v/v), to give (2S)-2-[(4S,5S)-3-benzyloxycarbonyl-4-cyclohexylmethyl-2,2-dimethyl-1,3-oxazolidin-5-yl]-methyl-N,3-dimethylbutanamide (B) [the less polar product], as a clear oil (211 mg); NMR (CDCl$_3$): 0.9 (d, b 6H), 1.1–2.0 (complex m, 23H), 2.8 (d, 3H), 3.7 (m, 2H), 5.1 (dd, 2H), 5.5 (br, 1H), 7.35 (m, 5H).

(b) Using a similar procedure to that described in Example 1(j), ammonium formate (101 mg) was added to a mixture of amide B (182 mg) and 10% palladium on charcoal catalyst (90 mg) in water/ethanol (1:9 v/v; 10 ml) to give, after work-up, (2S,4S,5S)-5-amino-6-cyclohexyl-4-hydroxy-2-isopropyl-N-methylhexanamide (A), as an oil (115 mg), which was used without further purification or characterisation.

EXAMPLE 8

A solution of sodium 8-propyl-6-(3-pyridyl)-1,2,4-triazolo[4,3-a]pyrazin-3-ylacetate (81 mg) in water (1 ml) was added to a solution of (2R,4S,5S)-5-amino-6-cyclohexyl-4-hydroxy-N,2-dimethylhexanamide (A) (55 mg) in DMF (9 ml). HOBT (33.7 mg) and EDAC (96 mg) were added and the solution was left to stand overnight. The reaction mixture was worked up by a similar procedure to that described in Example 1, followed by flash chromatography eluting with methanol/dichloromethane (1:9 v/v) to give (2R,4S,5S)-6-cyclohexyl-4-hydroxy-N,2-dimethyl-5-[8-propyl-6-(3-pyridyl)-1,2,4-triazolo[4,3-a]pyrazin-3-yl]acetamidohexanamide, as a foam (27 mg); NMR (400 MHz, d$_6$-DMSO/d$_4$-acetic acid): 0.7–1.7 (complex m, 21H), 2.0 (m, 2H), 2.5 (m, 1H), 2.55 (s, 3H), 3.3 (t, 2H), 3.4 (m, 1H), 3.8 (m, 1H), 4.3 (m, partially exchanged with d$_4$-acetic acid), 7.6 (dd, 1H), 8.5 (m, 1H), 8.7 (dd, 1H), 9.0 (s, 1H), 9.3 (dd, 1H); mass spectrum (+ve FAB, DMSO/glycerol): 536 (M+H)$^+$, 505, 297, 280; microanalysis, found: C, 62.3; H, 7.4, N, 17.6%; $C_{29}H_{41}N_7O_3 \cdot H_2O$ requires : C, 62.9, H, 7.8; N, 17.7%.

The starting material A was obtained as follows:

(a) Using an analogous procedure to that described in Example 1(h), but starting from (5R,4S)-3-benzyloxycarbonyl-4-cyclohexylmethyl-5-iodomethyl-2,2-dimethyl-1,3-oxazolidine (0.94 g) and propionic acid (0.74 g), together with proportionate quantities of the other necessary reagents, there was obtained crude (2RS)-3-[(4S,5S)-3-benzyloxycarbonyl-4-cyclohexylmethyl-2,2-dimethyl-1,3-oxazolidin-5-yl]-2-methylpropionic acid (B), as a clear oil (0.88 g), which was used without further purification or characterisation.

(b) Using an analogous procedure to that described in Example 7(a), but starting from the crude carboxylic acid B (0.88 g) and proportionate quantities of the other necessary reagents, there was first obtained, after purification by flash chromatography eluting with ethyl acetate/hexane (1:1 v/v), (2R)-3-[(4S,5S)-3-benzyloxycarbonyl-4-cyclohexylmethyl-2,2-dimethyl-1,3-oxazolidin-5-yl]-N,2-dimethylpropionamide (C), as a clear oil (230 mg); NMR (CDCl$_3$): 0.8–2.0 (complex m, 24H), 2.5 (m, 1H), 2.8 (d, 3H), 3.7 (m, 1H), 5.1 (dd, 1H), 5.6 (br, 1H), 7.35 (m, 5); and then (2S)-3-[(4S,5S)-3-benzyloxycarbonyl-4-cyclohexylmethyl-2,2-dimethyl-1,3-oxazolidin-5-yl]-N,2-dimethylpropionamide, as a clear oil (236 mg); NMR (CDCl$_3$); 0.8–2.0 (complex m, 24H), 2.5 (m, 1H), 2.8 (d, 3H), 3.7 (m,1H), 3.95 (m, 1H), 5.1 (dd, 1H), 5.4 (br, 1H), 7.35 (m, 5H).

(c) Using an analogous procedure to that described in Example 1(j), but starting from amide C (225 mg) and proportionate quantities of the other necessary reagents, there was obtained (2R,4S,5S)-5-amino-6- cyclohexyl-4-hydroxy-N,2-dimethylhexanamide (A), as an oil (130 mg), which was used without further purification or characterisation.

EXAMPLE 9

Using an analogous procedure to that described in Example 8, but starting from (2S,4S,5S)-5-amino-6-cyclohexyl-4-hydroxy-N-2-dimethylhexanamide (A) (45 mg) and proportionate quantities of the other necessary reagents, there was obtained (2S,4S,5S)-6-cyclohexyl-4-hydroxy-N,2-dimethyl-5-([8-propyl-6-(3-pyidyl)-1,2,4-triazolo[4,3-a]pyrazin-3-yl]acetamido)hexanamide, as a glassy solid (15 mg); NMR (d$_6$-DMSO/d$_4$-acetic acid): 0.7-1.7 (complex m, 21H), 2.0 (m, 2H), 2.4 (m, 1H), 2.6 (s, 3H), 3.3 (t, 2H), 3.45 (m, 1H), 3.9 (m, 1H), 4.3 (m, partially exchanged with d$_4$-acetic acid), 7.6 (dd, 1H), 8.5 (m, 1H), 8.7 (dd, 1H), 9.0 (s, 1H), 9.5 (dd, 1H); mass spectrum (+ve FAB, DMSO/m-nitrobenzyl alcohol: 536 (M+H)$^+$, 505, 297, 280.

The starting material A was obtained as follows:

Using an analogous procedure to that described in Example 1(j), but starting from (2S)-3-[(4S,5S)-3-benzyloxycarbonyl-4-cyclohexylmethyl-2,2-dimethyl-1,3-oxazolidin-5-yl]-N,2-dimethyl-propionamide (70 mg) and proportionate quantities of the other necessary reagents, there was obtained (2S, 4S, 5S)-5-amino-6-cyclohexyl-4-hydroxy-N,2-dimethylhexanamide (A), as an oil (45 mg), which was used without further purification or characterisation.

EXAMPLE 10

Using an analogous procedure to that described in Example 6, but starting from (2R,4S,5S)-5-amino-6-cyclohexyl-4-hydroxy-N,2-dimethylhexanamide (80 mg) and proportionate quantities of the other necessary reagents, there was obtained, after purification by flash chromatography eluting with methanol/dichloromethane (8:92 v/v), the two possible diastereoisomers of (2S,4S,5S)-6-cyclohexyl-4-hydroxy-N,2-dimethyl-5-[(2RS)-2-(8-propyl-6-(3-pyridyl)-1,2,4-triazolo[4,3-a]pyrazin-3-yl)-3-(3-pyridyl)propionamido]hexanamide, one as the less polar product, isolated as a foam (38 mg); NMR (d$_6$-DMSO/d$_4$-acetic acid): 0.5 (d, 3H), 0.6-1.7 (complex m, 18H), 2.0 (m,2H), 2.1 (m, 1H), 2.4 (s, 3H), 3.15 (dd, 1H), 3.2 (t, 3H), 3.4 (dd, 1H), 3.6 (m, 1H), 3.8 (m, 1H), 4.9 (dd, 1H), 7.35 (dd, 1H), 7.55 (dd, 1H), 7.8 (d, 1H), 8.45 (m, 2H), 8.6 (m, 2H), 9.2 (s, 1H), 9.3 (d, 1H); mass spectrum (+FAB, DMSO/glycerol): 627 (M+H)$^+$, 6709, 596, 388, 371, 343, 280; and the other as the more polar product, isolated as a foam (25 mg); NMR (d$_6$-DMSO/d$_4$-acetic acid): 0.7-1.5 (complex m, 21H), 2.0 (m, 2H), 2.4 (m, 1H), 2.6 (s, 3H), 3.2 (m, 2H), 3.35 (m, 2H), 3.8 (m, 1H), 3.9 (m, 1H), 4.8 (dd, 1H), 7.4 (dd, 1H), 7.6 (dd, 1H), 7.8 (d, 1H), 8.5 (m, 2H), 8.6 (m, 2H), 9.3 (d and s, 2H); mass spectrum (+FAB, DMSO/glycerol): 627 (M+H)$^+$, 609, 596, 388, 371, 343, 280; both isomers having an unknown, but opposite, configuration at the carbon atom linked to the 1,2,4-triazolo[4,3-a]pyrazine nucleus.

EXAMPLE 11

Using an analogous procedure to that described in Example 8, but starting from (2RS,4S,5S)-5-amino-N-butyl-6-cyclohexyl-4-hydroxy-2-methylhexanamide (A) (120 mg) and proportionate quantities of the other necessary reagents, there was obtained (2RS,4S, 5S)-N-butyl-6-cyclohexyl-4-hydroxy-2-methyl-5-([8-propyl-6-(3-pyridyl)-1,2,4-triazolo[4,3-a]pyrazin-3-yl]acetamido)hexanamide, as a glassy solid (20 mg); NMR (d$_6$-DMSO/d$_4$-acetic acid): 0.7-1.7 (complex m, 28H), 2.0 (m, 2H), 2.4 (m, 1H), 3.0 (m, 2H), 3.25 (t, 2H), 3.4 (m, 1H), 3.75 and 3.9 (both m, ratio 1:1, total 1H), 4.3 (m, partially exchanged with d$_4$-acetic acid), 7.55 (dd, 1H), 8.45 (m, 1H), 8.65 (dd, 1H), 9.0 (m, 1H), 9.3 (s, 1H); mass spectrum (+FAB, DMSO/glycerol): 578 (M+H)$^+$, 560, 505, 280; microanalysis, found: C, 65.1; H, 8.2; N, 16.6%; C$_{32}$H$_{47}$N$_7$O$_3$.0.5H$_2$O requires: C, 65.5; H, 8.2; N, 16.7%.

The starting material A was obtained as follows:

(a) Using an analogous procedure to that described in Example 1(i), but starting from crude (2RS)-3-[(4S,5S)-3-benzyloxycarbonyl-4-cyclohexylmethyl-2,2-dimethyl-1,3-oxazolidin-5-yl]-2-methylpropionic acid (1.05 g) and proportionate quantities of the other necessary reagents, there was obtained (2RS)-3-[(4S,5S)-3-benzyloxycarbonyl-4-cyclohexylmethyl-2,2-dimethyl-1,3-oxazolidin-5-yl]-N-butyl-2-methylpropionanamide (B), as a clear oil (160 mg) [after purification by flash chromatography eluting with ethyl acetate/hexane (3:7 v/v)]; NMR (CDCl$_3$): 0.9 (t, 3H), 1.0-2.0 (complex m, 19H), 2.4 (m, 1H), 3.25 (m,2H), 3.7 (m, 1H), 3.8 and 3.9 (both m, ratio 1:1, total 1H); 5.1 (m,2H), 5.4 and 5.7 (both br, ratio 1:1, total 1H), 7.35 (m, 5H).

(b) Using an analogous procedure to that described in Example 1(j), but starting from amide B (160 mg) and proportionate quantities of the other necessary reagents, there was obtained (2RS, 4S,5S)-5-amino-N-butyl-6-cyclohexyl-4-hydroxy-2-methylhexanamide (A), as an oil (120 mg), which was used without further purification or characterisation.

EXAMPLE 12

Using an analogous procedure to that described in Example 8, but starting from (4S,5S)-5-amino-N-butyl-6-cyclohexyl-4-hydroxy-2,2-dimethylhexanamide (A) (80 mg) and proportionate quantities of the other necessary reagents, there was obtained (4S,5S)-N-butyl-6-cyclohexyl-4-hydroxy-2,2-dimethyl-5-([8propyl-6-(3-pyridyl)-1,2,4-triazolo[4,3-a]pyrazin-3-yl]acetamido)hexanamide, as a glassy solid (20 mg); NMR (d$_6$-DMSO/d$_4$-acetic acid): 0.8-1.7 (complex m, 31H), 2.0 (m,2H), 3.0 (t, 2H), 3.25 (t, 2H), 3.5 (m, 1H), 3.75 (m, 1H), 4.3 (m, partially exchanged with d$_4$-acetic acid): 7.55 (dd, 1H), 8.45 (dt, 1H), 8.6 (m, 1H), 8.9 (s, 1H), 9.25 (m, 1H); mass spectrum (+FAB, DMSO/m-nitrobenzyl alcohol): 614 (M+Na)$^+$, 592 (M+H)$^+$, 574, 519, 405, 297, 280.

The starting material A was obtained as follows:

(a) Using an analogous procedure to that described in Example 1(h), but starting with iso-butyric acid (550 mg) and proportionate quantities of the other necessary reagents, and without the addition of HMPA, there was obtained 3-[(4S,5S)-3-benzyloxycarbonyl-4-cyclohexylmethyl-2,2-dimethyl-1,3-oxazolidin-5-yl]-2,2-dimethylpropionic acid (B), as a clear oil (650 mg), which was used without further purification or characterisation.

(b) Using an analogous procedure to that described in Example 1(i), but starting from crude carboxylic acid B (650 mg) and proportionate quantities of the other necessary reagents, there was obtained 3-[(4S,5S)-3-benzyloxycarbonyl-4-cyclohexylmethyl-2,2-dimethyl-1,3-oxazolidin-5-yl]-N-butyl-2,2-dimethylpropionamide (C), as a clear oil (120 mg); NMR (CDCl$_3$): 1.0 (t, 3H), 1.1-1.8 (complex m, 34H), 3.3 (m, 2H), 3.75 (m, 1H), 4.0 (m, 1H), 5.2 (dd, 2H), 7.4 (m, 5H).

(c) Using an analogous procedure to that described in Example 1(j), but starting from amide (C) (120 mg) and proportionate quantities of the other necessary reagents, there was obtained (4S,5S)-5-amino-N-butyl-6-cyclohexyl-4-hydroxy-2,2-dimethylhexanamide (A), as an oil (80 mg), which was used without further purification or characterisation.

EXAMPLE 13

Using an analogous procedure to that described in Example 6, but starting from (2S,4S,5S)-5-amino-6-cyclohexyl-4-hydroxy-2-isopropyl-N-(2-methoxyethyl)hexanamide (A) (80 mg) and proportionate quantities of the other necessary reagents, there was obtained, after purification by flash chromatography eluting with methanol/dichloromethane (8:92 v/v), (2S,4S,5S)-6--cyclohexyl-4-hydroxy-2-isopropyl-N-(2-methoxyethyl)-5-[(2RS)-2-(8-propyl-6-(3-pyridyl)-1,2,4-triazolo[4,3-a]pyrazin-3-yl)-3-(3-pyridyl)-propionamido]hexanamide, as a foam (40 mg); NMR (d$_6$-DMSO/d$_4$-acetic acid): 0.2-1.8 (complex m, 25H), 2.0 (m, 3H), 3.00-3.4 (complex m, 11H), 3.7 (m, 1H) 3.8 (m, 1H), 4.8 (m, 1H), 7.4 (m, 1H), 7.6 (m, 1H), 7.8 (m, 1H), 8.5 (m, 2H), 8.7 (m, 2H), 9.3 (m, 2H); mass spectrum (+ve FAB, DMSO/m-nitrobenzyl alcohol): 699 (M+H)$^+$, 624.

The starting material (A) was obtained as follows:

(a) Using an analogous procedure to that described in Example 1(i), but starting from crude (2RS)-2-[(4S,5S)-3-benzyloxycarbonyl-4-cyclohexylmethyl-2,2-dimethyl-1,3-oxazolidin-5-yl]methyl-3-methylbutanoic acid (1.11 g) and 2-methoxyethylamine (188 mg), together with proportionate quantities of the other necessary reagents, there was obtained, after purification by flash chromatography eluting with ethyl acetate/hexane (1:4 v/v), (2S)-2-[(4S,5S)-3-benzyloxycarbonyl-4-cyclohexylmethyl-2,2-dimethyl-1,3-oxazolidin-5-yl]methyl-N-(2-methoxyethyl)-3-methylbutanamide (B) [the less polar product], as a clear oil (285 mg); NMR (CDCl$_3$): 0.9 (d, 6H), 1.1-1.9 (complex, m, 22H), 2.1 (m, 1H), 3.35 (S, 3H), 3.5 (m, 4H), 3.7 (m, 2H), 5.1 (dd, 2H), 6.0 (br, 1H), 7.4 (m, 5H).

(b) Using an analogous procedure to that described in Example 1(j), but starting from amide B (130 mg) and proportionate quantities of the other necessary reagents, there was obtained (2S,4S,5S)-5-amino-6-cyclohexyl-4-hydroxy-2-isopropyl-N-(2-methoxyethyl)hexanamide (A), as an oil (82 mg), which was used without further purification or characterisation.

EXAMPLE 14

Using an analogous procedure to that described in Example 6, but starting from (2S,4S,5S)-5-amino-6-cyclohexyl-4-hydroxy-2-isopropyl-N-(2,2-dimethyl-3-dimethylaminopropyl)hexanamide (A) (109 mg) and proportionate quantities of the other necessary reagents, there was obtained, after purification by flash chromatography eluting with methanol/dichloromethane (1:4 v/v), (2S,4S,5S)-6-cyclohexyl-4-hydroxy-2--isopropyl-N-(2,2-dimethyl-3-dimethylaminopropyl)-5-[(2RS)-2-(8-propyl-6-(3-pyridyl)-1,2,4-triazolo[4,3a]-pyrazin-3-yl)-3-(3-pyridyl)propionamido]hexanamide as a foam (44 mg); NMR (d$_6$-DMSO/d$_4$-acetic acid): 0.5-2.1 (complex m, 34H), 2.7-3.5 (complex m, 14H), 3.7 (m, 1H), 3.9 (m, 1H), 4.9 (m, 1H), 7.4 (m, 1H), 7.6 (m, 1H), 7.8 (m, 1H), 8.5 (m, 2H), 8.7 (m, 2H), 9.3 (m, 2H); mass spectrum (+ve FAB, DMSO/m-nitrobenzyl alcohol): 754 (M+H)$^+$.

The starting material A was obtained as follows:

(a) Using an analogous procedure to that described in Example 1(i), but starting from crude (2RS)-2-[(4S,5S)-3-benzyloxycarbonyl-4-cyclohexylmethyl-2,2-dimethyl-1,3-oxazolidin-5-yl]methyl-3-methylbutenoic acid (620 mg) and 2,2-dimethyl-3-dimethylaminopropylamine (163 mg), together with proportionate quantities of the other necessary reagents, there was obtained, after purification by flash chromatography eluting with ethyl acetate/hexane (4:1 v/v), (2S)-2-[(4S,5S)-3-benzyloxycarbonyl-4-cyclohexylmethyl-2,2-dimethyl-1,3-oxazolidin-5-yl]methyl-N-(2,2-dimethyl-3-dimethylaminopropyl)-3-methylbutanamide (B) [the less polar product] (158 mg) as a clear oil; NMR (CDCl$_3$): 0.9 (s, 12H), 1.1-2.0 (m, 23H), 2.3 (m, 8H), 3.2 (m, 2H), 3.7 (m, 1H), 3.8 (m, 1H), 5.1 (dd, 2H), 7.4 (m, 5H).

(b) Using an analogous procedure to that described in Example 1(j), but starting from amide B( 150 mg), and proportionate quantities of the other necessary reagents, there was obtained (2S,4S,5S)-5-amino-6-cyclohexyl-4-hydroxy-2-isopropyl-N-(2,2-dimethyl-3-dimethylaminopropyl)hexanamide (A) as a clear oil (107 mg), which was used without further purification or characterisation.

EXAMPLE 15

A solution of N-[2-cyclohexyl-1-(S)-[(3S,5S)-2,3,4,5-tetrahydro-3-isopropyl-2-oxofur-5-yl]ethyl]-(2RS)-2-[8-propyl-6-(3-pyridyl)-1,2,4-triazolo[4,3-a]pyrazin-3-yl]-3-(3-pyridyl)propanamide (A) (256 mg) in 2-dimethylaminoethylamine (5 ml) and dioxan (5 ml) was heated at 100° C. for 6 hours. Volatile material was removed by evaporation and the residue dissolved in chloroform (20 ml). The solution was washed with water (4×10 ml), followed by saturated sodium chloride solution (10 ml), and dried (MgSO$_4$). The solvent was removed by evaporation and the residue was purified by flash chromatography eluting with methanol/dichloromethane (1:9 v/v gradually changing to 4:6 v/v). There was thus obtained the two possible diastereoisomers of (2S,4S,5S)-6-cyclohexyl-4-hydroxy-2-isopropyl-N-(2-dimethylaminoethyl)-5-[(2RS)-2-(8-propyl-6-(3-pyridyl)-1,2,4-triazolo[4,3-a]pyrazin-3-yl)-3-(3-pyridyl)propionamido]hexanamide, one as the less polar product, isolated as a white powder (91 mg) after trituration with ether; NMR (d$_6$-DMSO/d$_4$-acetic acid): 0.3(d, 3H), 0.5 (d, 3H), 0.6-1.8 (complex m, 20H), 2.0 (m, 2H), 2.8 (s+m, 7H), 2.9 (m, 1H), 3.0-3.4 (complex m, 6H), 3.6 (m, 1H), 3.9 (m, 1H) 4.8 (dd, 1H), 7.4 (dd, 1H), 7.6 (dd, 1H), 7.8 (d, 1H), 8.5 (m, 2H), 8.65 (m, 2H), 9.3 (s, 1H), 9.35 (d, 1H); mass spectrum (+ve FAB, DMSO/glycerol): 712 (M+H)$^+$, 624, 496, 388, 371, 343, 280; microanalysis, found: C, 62.0; H, 7.4; N, 15.9%; C$_{40}$H$_{57}$N$_9$O$_3$.3H$_2$O requires: C, 62.7; H, 8.2; N, 16.5%; and the other as the more polar product, isolated as a white power (107 mg) after trituration with ether; NMR (d$_6$-DMSO/d$_4$-acetic acid): 0.7-1.8 (complex m, 26H), 2.0 (m, 2H), 2.8 (s, 67H), 3.1-3.5 (complex m, 8H), 3.7 (m, 1H), 3.9 (m, 1H), 4.85 (dd, 1H), 7.4 (dd, 1H), 7.6 (dd, 1H), 7.8 (m, 1H), 8.5 (m, 2H), 8.65 (m, 2H), 9.3 (d+s, 2H); mass spectrum (+ve FAB, DMSO/m-nitrobenzyl alcohol): 712 (M+H)$^+$, 624; microanalysis, found: C, 64.7; H, 7.8; N, 16.8%; c$_{40}$H$_{57}$N$_9$O$_3$.2H$_2$O requires: C, 64.3; H, 8.2; N, 16.9%; both isomers having an unknown, but opposite, configuration at the carbon atom linked to the 1,2,4-triazolo[4,3-]pyrazine nucleus.

The starting material A was obtained as follows:

(a) A solution of (3S,5S)-5-[(1S)-(1-azido-2-cyclohexyl)ethyl-3-isopropyl]tetrahydro]2-furanone (obtained as described in European Patent 0258183) (2.69 g) in ethanol (50 ml) was hydrogenated over 10% palladium on carbon catalyst (280 mg) at 1 atmosphere pressure. After uptake of hydrogen had ceased, the catalyst was removed by filtration through diatomaceous earth and the filtrate was evaporated to give (3S,5S)-5-[(1S)-1-amino-2-cyclohexyl)ethyl-3-isopropyl]tetrahydro-2-furanone (B) (2.48 g), m.p. 47°-48° C. (from hexane); NMR (CDCl$_3$): 0.8-1.9 (complex m, 19H), 2.1 (m, 3H), 2.6 (ddd, 1H), 2.85 (1H, m), 4.2(1H), m).

(b) A solution of sodium 2-[8-propyl-6-(3-pyridyl)-1,2,4-triazolo[4,3-a]pyrazin-3-yl]-3-(3-pyridyl)propionate (3.95 g) in water (10 ml) was added to a solution of the amine B (2.48 g) in DMF (90 ml). HOBT (1.30 g) and EDAC (1.85 g) were added and the solution was allowed to stand for 18 hours. Volatile material was removed by evaporation and the residue partitioned between ethyl acetate (200 ml) and saturated sodium hydrogen carbonate solution (200 ml). The organic phase was separated and washed with water (200 ml), followed by saturated sodium chloride solution (200 ml).

The organic phase was dried (MgSO$_4$) and the solvent was removed by evaporation. The residue was purified by flash chromatography, eluting with methanol/dichloromethane (1:9 v/v), to give N-[2-cyclohexyl-1-(S)-[(3S,5S)-2,3,4,5-tetrahydro-3-isopropyl-2-oxofur-5-yl]ethyl-(2RS)-2-[8-propyl-6-(3-pyridyl)-1,2,4-trizolo[4,3-a]pyrazin-3-yl]-3-(3-pyridyl)propionamide (A), as a white powder (4.14 g), m.p. 200°-202° C. (after trituration with ether); NMR (d$_6$-DMSO/d$_4$-acetic acid): 0.6 (d, 6H), 0.7-1.9 (complex m, 20H), 2.0 (m, 2H), 3.4 (m, 3H), 3,9 (m, 2H), 4.3 (m, 1H), 4.85 (m, 1H), 7.4 (m, 1H), 7.6 (m, 1H), 7.9 (m, 1H), 8.5 (m, 2H), 8.7 (m, 2H), 9.1, 9.3 (both s, ratio 1:1, total 1H), 9.3, 9.35 (both d, ratio 1:1, total 1H.

EXAMPLES 16-22

Using an analogous procedure to that described in Example 15, but starting from the appropriately substituted primary amine of the formula $R^8.NH_2$ in place of 2-dimethylaminoethylamine, the following compounds of the formula I wherein $R^1$=propyl, $R^2$=3-pyridyl, $R^3$=(3-pyridyl)methyl, $R^4$=cyclohexylmethyl, $R^6$=isopropyl and $R^5$ and $R^7$ are both hydrogen, and wherein the chiral centres of the fragment of the structure:

—CO.NH.CH($R^4$).CH(OH).CH$_2$.C($R^5$)($R^6$)—in the said compounds have the S-configuration, were obtained in yields of 19 to 79% having the NNR and mass spectral data* shown:

(Example 16)

$R^8$=2-aminoethyl;

less polar diastereoisomer, NMR: 0.6 (d, 3H), 0.7 (d, 3H), 0.7-1.8 (complex m, 19H), 2.0 (m, 3H), 2.9 (t, 2H), 3.2-3.6 (complex m, 7H), 3.8 (m, 1H, 4.6 (m, 1H), 7.3 (dd, 1H), 7.6 (dd, 1H), 7.8 (d, 1H), 8.5 (m, 3H), 8.65 (dd, 1H), 9.3 (d, 1H), 9.5 (s, 1H); mass spectrum: 684 (M+H)$^+$; more polar diastereoisomer, NMR: 0.6-1.8 (complex m,25H), 2.0 (m, 3H), 3.0 (t, 2H), 3.2-3.6 (complex m, 7H), 3.8 (m, 1H), 4.9 (m, 1H), 7.4 (dd, 1H), 7.6 (dd, 1H), 7.9 (m, 1H), 8.5 (m, 3H), 8.65 (dd, 1H, 9.35 (d and s, 2H); mass spectrum: 684 (M+H)$^+$;

(Example 17)

$R^8$=3-aminopropyl;

isolated as a 1:1 mixture of diastereoisomers**, NMR: 0.2-2.1(complex m, 30H), 2.7 (m, 2H), 3.2 (m, 6H), 3.6 (m, 1H), 3.85 (m, 1H), 4.8 (m, 1H), 7.35 (m, 1H), 7.55 (m, 1H), 7.8 (m, 1H), 8.5 (m, 2H), 8.6 (m, 2H), 9.3 (m, 2H); mass spectrum: 698 (M+H)$^+$;

(Example 18)

$R^8$=3-pyridylmethyl;

isolated as 1:1 mixture of diastereoisomers, NMR; 0.2-1.8 complex m, 25H), 2.0 (m, 3H), 3.1-3.5 (complex m, 2H), 3.6-3.9 (complex m, 2H), 4.2 and 4.4 (both S, ratio 1:1, total 2H), 4.8 (m, 1H), 7.3 (m,3H), 7.7 (m, 3H), 8.45 (m, 3H), 8.6 (m, 2H), 9.3 (m, 2H); mass spectrum: 732 (M+H)$^+$;

(EXAMPLE 19

$R^8$=2-(N-morpholino)ethyl;

isolated as a 1:1 mixture of diastereoisomers, NMR: 0.3-1.8 (complex m, 25H), 2.0 (m, 3H), 2.8-3.9 (complex m, 18H), 4.8 (m, 1H), 7.4 (m, 1H), 7.6 (m, 1H), 7.9 (m, 1H), 8,5 (m, 2H), 8.65 (m, 2H), 9.25 (two singlets, ratio 1:1, 1H), 9.3 (m, 1H); mass spectrum : 754(M+H)$^+$;

(EXAMPLE 20)

$R^8$=2-(N-piperazinyl)ethyl;

isolated as a 1:1 mixture of diastereoisomers**, NMR: 0.2-1.8 (complex m, 25H), 2.0 (m, 3H), 2.6 (m, 4H), 2.9-3.5 (complex m, 12H), 3.6 (m, 1H), 3.8 (m, 1H), 4.8 (m, 1H), 7.3 (m, 1H), 7.6 (m, 1H), 7.8 (m, 1H), 8.45 (m, 2H), 8.6 (m, 2H), 9.3 (m, 2H); mass spectrum; 753(M+H)$^+$;

Example 21)

$R^8$=4-hydroxybutyl;

less polar diastereoisomer, NMR: 0.2 (d, 3H), 0.4 (d, 3H), 0.5-1.7 (complex m, 23H), 2.0 (m, 3H), 2.8-3.4 (complex m, 8H), 3.6 (m, 1H), 3.8 (m, 1H), 4.8 (dd, 1H), 7.3 (dd, 1H), 7.5 (dd, 1H), 7.7 (m, 1H), 8.4 (m, 2H), 8.6 (m, 2H), 9.15 (s, 1H), 9.3 (d, 1H); mass spectrum: 713 (M+H)$^+$; more polar diastereoisomer, NMR: 0.5-1.7 (complex m, 29H), 2.0 (m, 3H), 3.0-3.6 (complex m, 8H), 3.7 (m, 1H), 3.8 (m, 1H), 4.84 (dd, 1H) 7.35 (dd, 1H), 7.6 (dd, 1H), 7.85 (m, 1H), 8.5 (m, 2H), 8.7 (m, 2H), 9.2 (s, 1H), 9.25 (d, 1H); mass spectrum 713(M+H)$^+$; and (Example 22)

$R^8$=2-hydroxyethyl;

isolated as a 1:1 mixture of diastereoisomers, NMR: 0.2-1.7 (complex m, 25H), 2.0 (m, 3H), 3.0-3.5 (complex m, 8H), 3.65 (m, 1H, 3.8 (m, 1H), 4.8 (m, 1H), 7.3 (m, 1H), 7.6 (m, 1H), 7.8 (m, 1H), 8.4 (m,2H), 8.6 (m, 2H), 9.3 (m, 2H),; mass spectrum: 685(M'H)$^+$. [*NMR spectra were obtained using d$_6$-DMSO/d$_4$-acetic acid as solvent; and mass spectra were obtained using +ve FAB. ** In Examples 16, 17 and 20, flash chromatographic purification of the products was carried out by eluting with a mixture of aqueous ammonia/methanol/dichloromethane in the ratios 1:19:180, 1:9:90 and 1:19:80 v/v respectively.]

Example 23

A 1 M solution of dimethylaluminium chloride in hexane (1.4 ml) was added to a stirred solution of N-methylbutylamine (0.17 ml) in dry dichloromethane (10 ml) at 0° C. under an atmosphere of argon. The temperature was maintained at 0° C. for 15 minutes and then a solution of N-[2-cyclohexyl-1-(S)-(3S,5S)-2,3,4,5-tetrahydro-3-isopropyl-2-oxofur-5-yl]ethyl-(2RS)-2-[8-propyl-6-(3-pyridyl)-1,2,4-triazolo[4,3-a]pyrazin-3-yl]-3-(3-pyridyl)propanamide (220 mg) in dry dichloromethane (10 ml) was added. The solution was heated under reflux for 6 hours, and then aqueous pH7 phosphate buffer solution (20 ml) was added. The organic layer was separated, washed with saturated sodium chloride solution (20 ml) and dried (MgSO$_4$). The solvent was removed by evaporation and the residue purifed by flash chromatography, eluting with methanol/dichloromethane (3:97 v/v gradually changing to 1:9 v/v), to give (2S,4S,5S)-N-butyl-6-cyclohexyl-4-hydroxy-2-isopropyl-N-methyl-5-[(2RS)-2-(8-propyl-6-(3-pyridyl)-1,2,4-triazolo[4,3-a]pyrazin-3-yl)-3-(3-pyridyl)propionamido]hexanamide, isolated as a white powder (50 mg) after trituration with ether; NMR (d$_6$DMSO/d$_4$ acetic acid): 0.2–1.7 (complex m, 32H), 2.0 (m, 3H), 2.5–3.5 (complex m, 9H), 3.65 (m, 1H), 3.8 (m, 1H), 4.8 (m, 1H), 7.4 (m, 1H), 7.6 (m, 1H), 7.9 (m, 1H), 8.5 (m, 2H), 8.7 (m, 2H), 9.3 (m, 2H); mass spectrum (+ve FAB DMSO/m-nitrobenzyl alcohol): 711(M+H)+, 624, 343, 280.

EXAMPLES 24–26

Using an analogous procedure to that described in Example 23, but starting from the appropriately substituted secondary amine of the formula R$^7$R$^8$NH in place of N-methylbutylamine, the following compounds of the formula I wherein R$^1$=propyl, R$^2$=3-pyridyl, R$^3$=(3-pyridyl)methyl, R$^4$=cyclohexylmethyl, R$^5$=hydrogen and R$^6$=isopropyl, and wherein the chiral centers of the fragment of the structure —CO.NH.CH(R$^4$).CH(OH).CH$_2$.C(R$^5$)(R$^6$)—in the said compounds have the S-configuration, were obtained as 1:1 mixtures of diastereoisomers in yields of 51–83%, having the NMR and mass spectral data* as shown:

(Example 24)

R$^7$=methyl, R$^8$=2-dimethylaminoethyl NMR: 0.3–1.7 (complex m, 25H), 2.0 (m, 3H, 2.8–4.0 (complex m, 17H), 4.85 (m, 1H), 7.5 (m, 1H), 7.65 (m, 1H), 7.9 (m, 1H), 8.5 (m, 2H), 8.7 (m, 2H), 9.1 and 9.25 (both s, ratio 1:1, total 1H), 9.3 and 9.35 (both d, ratio 1:1, total 1H); mass spectrum: 726 (M'H)+; [Flash chromatographic purification was carried out eluting with aqueous ammonia/methanol/dichloromethane (1:19:35 v/v)].

(Example 25)

R$^7$R$^8$N=morpholino

NMR: 0.2–1.7 (complex m, 25H), 2.0 (m, 2H), 2.2 and 2.7 (both m, ratio 1:1, total 1H), 3.1–3.8 (complex m, 13H), 3.9 (m, 1H), 4.9 (m, 1H), 7.4 (m, 1H), 7.6 (m, 1H), 7.9 (m, 1H), 8.5 (m, 2H), 9.2 and 9.25 (both s, ratio 1:1, total 1H), 9.3 and 9.4 (both d: ratio 1:1, total 1H); and

(Example 26)

R$^7$R$^8$N=N-methylpiperazinyl

NMR: 0.2–1.7 (complex m, 25H), 2.0 (m, 2H), 2.2 and 2.7 (both m, integration ratio 1:1, total 1H), 2.8 (2 singlets, 3H), 2.9–4.0 (complex m, 14H), 4.856 (m, 1H), 7.4 (m, 1H), 7.6 (m, 1H), 7.8 (d, 1H), 8.5 (m, 2H), 8.65 (m, 2H), 9.25 and 9.3 (both s, ratio 1:1, total 1H), 9.35 and 9.4 (both d, ratio 1:1, total 1H). [*NMR spectra were obtained using d$_6$-DMSO/d$_4$-acetic acid as solvent; mass spectra were obtained using +ve FAB]

EXAMPLE 27

A solution of (2S,4S,5S)-N-butyl-6-cyclohexyl-4-hydroxy-2-isopropyl-5-[3-(1-triphenylmethylimidazol-4-yl)-(2RS)-2-(8-propyl-6-(3-pyridyl)-1,2,4-triazolo[4,3-a]pyrazin-3-yl)propionamido]hexanamide (A) (187 mg) in trifluoroacetic acid (8 ml) and water (2 ml) was stirred for 75 minutes. Volatile material was removed by evaporation and saturated sodium hydrogen carbonate solution (10 ml) added to the residue. The mixture was extracted with chloroform (2×20 ml) and the combined extracts were washed successively with water (10 ml) and saturated sodium chloride solution (10 ml) and dried (MgSO$_4$). The solvent was removed by evaporation and the residue triturated with ether to give (2S,4S,5S)-N-butyl-6-cyclohexyl-4-hydroxy-5-[3-a]pyrazin-3-yl)propionamido]-2-isopropylhexanamide as a white powder (60 mg); NMR (d$_6$-DMSO/d$_4$-acetic acid): 0.3–1.7 (complex m, 32H), 2.0 (m, 3H), 2.9–3.9 (complex m, 8H), 4.9 (m, 1H), 7.3 (m, 1H), 7.6 (m, 1H), 8.5 (m, 2H), 8.7 (m, 1H), 9.25 and 9.35 (both S, ratio 1:1, total 1H), 9.3 (m, 1H); mass spectrum (+ve FAB, DMSO): 686 (M+H)+, 360, 332.

The starting material (A) was obtained as follows:

(a) Triphenylmethyl chloride (2.78 g) was added to 4-hydroxymethylimidazole hydrochloride (1.34 g) and triethylamine (2.8 ml) in dichloromethane (20 ml) stirred at 0° C. under an atmosphere of argon. The mixture was stirred for 18 hours and the insoluble solid was collected by filtration. The solid was washed well with water and dried under high vacuum to give 4-hydroxymethyl-1-triphenylmethyl-imidazole (B) as a white solid (2.4 g); NMR (90 MHz, d$_6$-DMSO): 4.3 (d, 2H), 4.8 (br t, 1H), 6.7 (S, 1H), 7.0–7.5 (complex m, 16H).

(b) Methanesulphonyl chloride (0.45 ml) was added dropwise to the hydroxymethyl compound B (1.0 g) and triethylamine (0.82 ml) in dichloromethane (20 ml) stirred at 0° C. under an atmosphere of argon. The mixture was stirred for 18 hours and then added to ice-cold saturated sodium hydrogen carbonate solution (20 ml). The organic phase was separated, washed with water (20 ml), followed by saturated sodium chloride solution (20 ml) and dried (MgSO$_4$). The solvent was removed by evaporation and the residue purified by flash chromatography, eluting with ethyl acetate/hexane (7:3 v/v), to give 4-chloromethyl-1-triphenylmethylimidazole (C), as a white foam (0.8 g) NMR (90 MHz, CDCl$_3$): 4.6 (s, 2H), 6.8 (s, 1H), 7.0–7.15 (complex m, 15H).

(c) The chloromethylimidazole C (394 mg) was added to a solution of ethyl 8-propyl-6-(3-pyridyl)-1,2,4-triazolo[4,3-a]pyrazin-3-ylacetate (325 mg) and tetrabutylammonium fluoride trihydrate (0.95 g) in DMF (5 ml). The solution was left to stand for 4 hours and then added to water (150 ml). The mixture was extracted with ethyl acetate (2×50 ml) and the extracts were washed successively with water (50 ml), saturated sodium chloride solution (50 ml) and dried (MgSO$_4$). The solvent was removed by evaporation and the residue purified by flash chromatography, eluting with ethyl acetate and gradually changing to methanol/ethyl acetate (1:19 v/v), to give ethyl 3-(1-triphenylmethylimidazol-4-yl)-2-[8-propyl-6-(3-pyridyl)-1,2,4-triazolo[4,3-a]pyrazin-3-yl]propionate (D), as a foam (300 mg); NMR (CDCl$_3$): 1.15 (t,3H), 1.2 (t, 3H), 2.1 (m, 2H), 3.3 (t, 2H), 3.6 (m, 2H), 5.0 (m, 1H), 6.5 (s, 1H), 6.9 m, 6H, 7.3 (m, 10H), 8.3 (m, 1H), 8.4 (s, 1H), 8.7 (dd, 1H), 9.2 (d, 1H).

(d) The ester D (290 mg) was hydrolysed with 1 M aqueous sodium hydroxide solution (0.46 ml) in ethanol (2 ml) using a similar procedure to that described in Example 3(b) to give sodium 3-(1-triphenylmethylimidazol-4-yl)-2-[8-propyl-6-(3-pyridyl)-1,2,4-triazolo [4,3-a]pyrazin-3-yl]propionate (E), as an off-white solid (280 mg), which was used without further purification or characterisation.

(e) Using an analogous procedure to that described in Example 3, but starting from sodium salt (E) (280 mg) and (3S,5S)-5-[(1S)-(1-amino-2-cyclohexyl)ethyl-3-isopropyl]tetrahydro-2-furanone (113 mg) and proportionate quantities of the other necessary reagents there was obtained N-[2-cyclohexyl-1-(S)-[(3S,5S)-2,3,4,5-tetrahydro-3-isopropyl-2-oxofur-5-yl]ethyl-3-(1-triphenylmethylimidazol-4-yl)-(2RS)-2-[8-propyl-6-(3-pyridyl)-1,2,4-trizolo[4,3-a]pyrazin-3-yl]propionamide (F), as a white power (280 mg); NMR (d$_6$-DMSO): 0.6–1.8 (complex m, 24H), 2.0 (m,4H), 3.3 (m, 4H), 4.0 (m, 1H), 4.4 (m, 1H), 4.85 (m, 1H), 6.55 and 6.65 (both s, ratio 1:1, total 1H), 6.9 (m, 6H), 7.15 and 7.2 (both s, ratio 1:1, total 1H), 7.3 (m, 9H), 7.5 (m, 1H), 8.2–8.5 (complex m, 2H), 8.65 (dd, 1H), 8.9 and 9.2 (both s, ratio 1:1, total 1H), 9.2 and 9.3 (both d, ratio 1:1, total 1H.

(f) Using an analogous procedure to that described in Example 5, compound F (269 mg) was heated under reflux in butylamine (5 ml) to give, after work up, (2S,4S,5S)-N-butyl-6-cyclohexyl-4-hydroxy-2-isopropyl-5-[3-(1triphenylmethylimidazol-4-yl)-(2RS)-2-(8-propyl-6-(3-pyridyl)-1,2,4-triazolo[4,3-a]pyrazin-3-yl)propionamido]hexanamide (A), as a white powder (192 mg); NMR (CDCl$_3$); 0.7–2.2 (complex m, 33H), 3.0–3.6 (complex m, 7H), 3.9 (m, 1H), 4.8 and 5.0 (both m, ratio 1:1, total 1H), 6.6 and 6.75 (both s, ratio 1:1, total 1H), 7.0 (m, 6H), 7.3 (m, 11H), 8.4 (m, 1H), 8.55 and 8.7 (both s, ratio 1:1, total 1H), 8.6 (m, 1H), 9.2 and 9.25 (both d, ratio 1:1, total 1H).

EXAMPLE 28

Using an analogous procedure to that described in Example 5, N-[1-(S)-[3R,5S)-3-butyl-2,3,4,5-tetrahydro-2-oxofur-5-yl]-2-cyclohexylethyl]--(2RS)-2-[8-propyl-6-(3-pyridyl)-1,2,4-triazolo[4,3-a]pyrazin-3-yl]-3-(3-pyridyl)propionamide (A) (332 mg) in butylamine (5 ml) gave (2R,4S,5S)-N,2-dibutyl-6-cyclohexyl-4-hydroxy-5-[(2RS)-2-(8-propyl-6-(3-pyridyl)-1,2,4-triazolo[4,3-a]pyrazin-3-yl)-3-(3-pyridyl)-propionamido]hexanamide as a solid (230 mg); NMR (d$_6$-DMSO/d$_4$-acetic acid): 0.2–1.7 (complex m, 34H), 1.9–2.3 (m, 3H), 2.6–3.5 (complex m, 6H), 3.6 (brd, 1H), 3.8 (m, 1H), 4.8 (m, 1H), 7.3 (m, 1H), 7.5 (m, 1H), 7.8 (m, 1H), 8.4 (m, 2H), 8.6 (m, 2H), 9,15 and 9,25 (both s, ratio 1:1, total 1H), 9.3 (d, 1H); mass spectrum (+ve FAB, methanol/m-nitrobenzyl alcohol: 733 (M+Na)$^+$, 711 (M+H)$^+$, 693, 638, 497, 395, 343, 288; microanalysis, found: C, 67.8; H, 8.1; N, 15.1%; C$_{41}$H$_{58}$ N$_8$O$_4$.H$_2$O requires: C, 67.55; H, 8.3; N, 15.4%.

The starting material A was obtained as follows:

(a) A 1.6 M solution of butyllithium in hexane (2.34 ml) was added dropwise over a period of 5 minutes to a stirred solution of hexamethyldisilazane (0.60 g) in dry THF (2 ml) at 0° C. under an atmosphere of argon. The solution was cooled to −78° C. and a solution of (5S)-5-[(1S)-(1-tert-butoxycarbonylamino-2-cyclohexyl)ethyl]-tetrahydro-2-furanone (obtained as described in European Patent No. 270234) (467 mg) in dry THF (2 ml) was added. The temperature was maintained at −78° C. for 15 minutes, and then a solution of transcrotyl bromide (243 mg) in dry THF (2 ml) was added. The solution was stirred at −78° C. for 1 hour and then a solution of acetic acid (0.3 ml) in THF (2 ml) was added. The mixture was allowed to warm to ambient temperature and saturated ammonium chloride solution (2 ml) and water (25 ml) were added. The mixture was extracted with ethyl acetate (3×25 ml). The combined extracts were washed with 1 M citric acid solution (3×5 ml), followed by saturated sodium chloride solution (4×10 ml) and dried (MgSO$_4$). The solvent was removed by evaporation and the residue purified by flash chromatography eluting with ether/hexane (1:2 v/v) to give (3R, 5S)-3-(2-butenyl)-5-[(1S)-(1-tert-butoxycarbonylamino-2-cyclohexyl)ethyl]tetrahydro-2-furanone (B), as a clear oil (269 mg); NMR (d$_6$-DMSO/d$_4$-acetic acid): 0.6–2.7 (complex m, 30H), 3.7 (m, 1H), 4.4 (m, 1H), 5.45 (m, 2H).

(b) A solution of compound B (201 mg) in ethyl acetate (10 ml) was hydrogenated over 10% palladium on charcoal catalyst at 1 atmosphere pressure. After uptake of hydrogen had ceased, the catalyst was removed by filtration through diatomaceous earth and the filtrate evaporated to give (3R,5S)-5-[(1S)-(1-tert-butoxycarbonylamino-2-cyclohexyl)ethyl]-3-butyltetrahydro-2-furanone (C) as a colourless viscous oil (186 mg); NMR (d$_6$-DMSO/d$_4$-acetic acid): 0.6–1.8 (complex m, 31H), 1.95 (m, 1H), 2.2 (m, 1H), 2.45 (m, 1H), 3.7 (m, 1H), 4.45 (m, 1H).

(c) Compound C (180 mg) was dissolved in a 8M solution of hydrogen chloride in dioxan (5 ml) and the solution was allowed to stand for 1 hour. Volatile material was removed by evaporation and the residue was dissolved in toluene (5 ml). The volatile material was again removed by evaporation and the same procedure repeated with two further 5 ml portions of toluene to give (3R,5S)-5-[(1S)-(1-amino-2-cyclohexyl)ethyl]-3-butyltetrahydro-2-furanone hydrochloride (D) as a foam (145 mg), which was used without purification or characterisation.

(d) A solution of sodium 2-[8-propyl-6-(3-pyridyl)-1,2,4-triazolo[4,3-z]pyrazin-3-yl]-3-(3-pyridyl)propionate (205 mg) in water (0.5 ml) was added to a solution of the amine hydrochloride D (145 mg) in DMF (4.5 ml). HOBT (77 mg) and DCC (124 mg) were added and the solution was allowed to stand for 18 hours. The solvent was removed by evaporation and the residue partitioned between saturated sodium bicarbonate solution (10 ml) and ethyl acetate (10 ml). Insoluble material was removed by filtration and the organic phase was separated. The solution was washed successively with saturated sodium bicarbonate solution (3×5 ml) and saturated sodium chloride solution (2×5 ml), and the dried (MgSO$_4$). The solvent was removed by evaporation to give N-[1-(S)-[(3R,5S)-3-butyl-2,3,4,5-tetrahydro-2-oxofur-5-yl]-2-cyclohexylethyl]-(2RS)-2-[8-propyl-6-(3-pyridyl)-1,2,4-triazolo[4,3-a]pyrazin-3-yl]-3-(3-pyridyl)-propionamide (A), as a foam (332 mg), which was used without purification or characterisation.

EXAMPLE 29-30

Using an analogous procedure to that described in Example 28, but starting from the appropriately substituted lactone of the formula VIII, the following compounds of the formula I wherein $R^1$=propyl, $R^2$=3-pyridyl, $R^3$=(3-pyridyl)methyl, $R^4$=cyclohexylmethyl, $R^5$ and $R^7$=hydrogen and $R^8$=butyl, and wherein the chiral centres of the fragment of the structure —CO.NH.CH($R^4$).CH(OH)— have the S-configuration and of the fragment of the structure —CH$_2$.C($R^5$)($R^6$)— have the R-configuration were obtained as 1:1 mixtures of diastereoisomers having the NMR and mass spectral data* as shown:

(EXAMPLE 29)

$R^6$=isobutyl

NMR: 0.1-1.7 (complex m, 34H), 1.9-2.4 (m, 3H), 2.8-3.55 (complex m, 6H), 3.65 (m, 1H), 3.8 (m, 1H), 4.85 (m, 1H), 7.35 (m, 1H), 7.55 (m, 1H), 7.8 (m, 1H), 8.4-8.6 (m, 2H), 8.65 (m, 2H), 9.15 and 9.25 (both s, ratio 1:1, total 1H), 9.35 (brd, 1H); mass spectrum: 711(m+H)$^+$; and (Example 30)

$R^6$=propyl;

NMR: 0.2-1.7 (complex m, 32H), 1.9-2.4 (m, 3H), 2.8-3.9 (complex m, 8H), 4.8 (m, 1H), 7.55 (m, 1H), 7.8 (m, 1H), 8.4-8.6 (m, 2H), 8.65 (m, 2H), 9.15 and 9.3 (both s, ratio 1:1, total 1H), 9.35 (m, 1H); mass spectrum; 697(M+H)$^+$. [*NMR spectra obtained using d$_6$-DMSO/d$_4$-acetic acid as solvent; mass spectra were obtained using +ve FAB]

The starting lactones of the formula VIII used in Examples 29 and 30 were obtained using analogous procedures to those described in Example 28, parts (a) to (d) but replacing trans-crotyl bromide in part (a) by 3-bromo-2-methylpropene in Example 29 and by 3-bromo-1-propene in Example 30. The intermediates formed in carrying out such procedures in Examples 29 and 30 had satisfactory NMR spectra and were used without further purification.

EXAMPLE 31

Using an analogous procedure to that described in Example 28, but starting from N-[1-(S)-[(3R,5S)-2,3,4,5-tetrahydro-3-methoxymethyl-2-oxofur-5-yl]-2-cyclohexylethyl]-(2RS)-2-[8-propyl-6-(3-pyridyl)-1,2,4-triazolo[4,3-a]pyrazin-3-yl]-3-(3-pyridyl)propionamide (A), there was obtained (2S,4S,5S)-N-butyl-6-cyclohexyl-4-hydroxy-2-methoxymethyl-5-[(2RS)-2-(8-propyl-6-(3-pyridyl)-1,2,4-triazolo]4,3-a]pyrazin-3-yl)-3-(3-pyridyl)propionamido]hexanamide; NMR (d$_6$-DMSO/d$_4$-acetic acid): 0.2-1.7 (complex m, 25H), 1.9-2.4 (complex m, 3H), 2.8-3.9 (complex m, 13H), 4.85 (m, 1H), 7.4 (m, 1H), 7.6 (m, 1H), 7.8 (m, 1H), 8,5 (m, 2H), 8.65 (m, 2H), 9.15 and 9.3 (both s, ratio 1:1, total 1H), 9.35 (m, 1H); mass spectrum (+ve FAB): 699 (M+H)$^+$.

The starting lactone A used in Example 31 was obtained using analogous procedures to those described in Example 28, parts (a), (c), and (d) but replacing trans-crotyl bromide in part (a) by bromomethyl methyl ether and carrying out the alkylation at −100° C. to −78° C. in the presence of 1,3-dimethyl-3,4,5,6-tetrahydro-2(1H)-pyrimidinone (DMPU; 4 equivalents). The intermediates formed in carrying out such procedures had satisfactory NMR spectra and were used without further purification.

EXAMPLE 32

(all parts by weight)

The compounds of the invention may be administered for therapeutic or prophylactic use to warm-blooded animals such as man in the form of conventional pharmaceutical compositions, typical examples of which include the following:

| a) Injectable Solution (for intravenous administration) | |
|---|---|
| Active ingredient* | 0.05-1.0 |
| Propylene glycol | 5.0 |
| Polyethylene glycol (300) | 3.0-5.0 |
| Purified water | to 100% |
| b) Injectable Suspension (for intramuscular administration) | |
| Active ingredient* | 0.05-1.0 |
| Methylcellulose | 0.5 |
| Tween 80 | 0.05 |
| Benzyl alcohol | 0.9 |
| Benzalkonium chloride | 0.1 |
| Purified water | to 100% |
| c) Capsule (for oral administration) | |
| Active ingredient* | 10 or 30 |
| Lactose powder | 588.5 or 568.5 |
| Magnesium stearate | 1.5 |
| b) Tablet (for oral administration) | |
| Active ingredient* | 25 |
| Microcrystalline cellulose | 415 |
| Starch (pregelatinised) | 57.5 |
| Magnesium stearate | 2.5 |

Note: the active ingredient * is typically an Example described hereinbefore and may conveniently be present as a pharmaceutically acceptable acid-addition salt such as the hydrochloride salt. Tablets and capsules may conveniently be coated in conventional manner in order modify or sustain dissolution of the active ingredient.

SCHEME 1

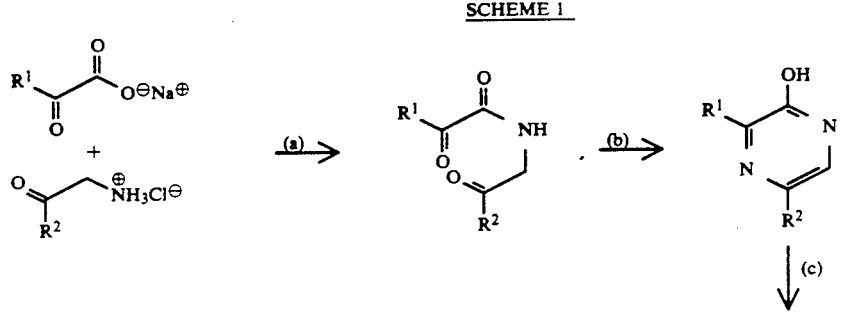

SCHEME 1

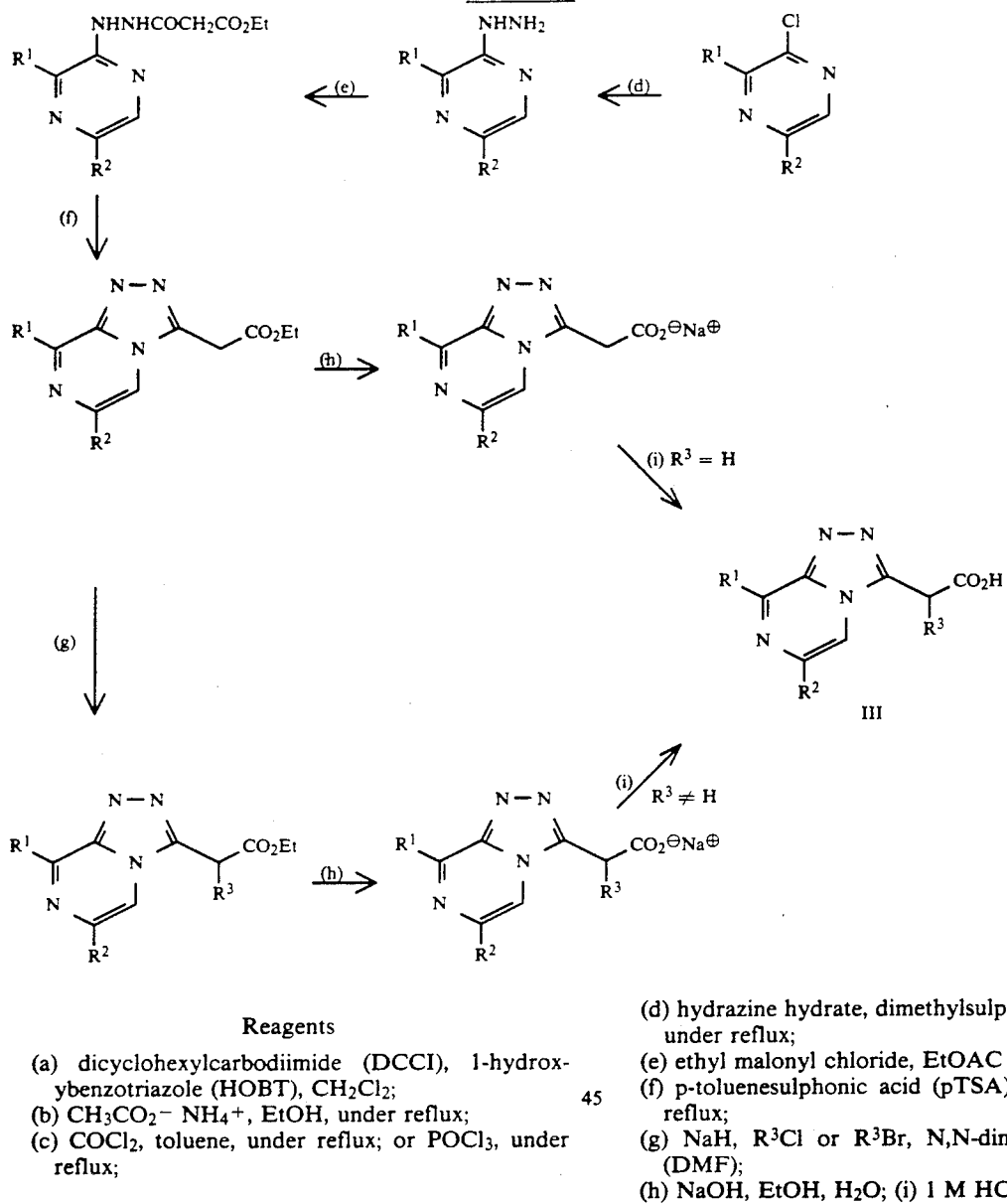

Reagents

(a) dicyclohexylcarbodiimide (DCCI), 1-hydroxybenzotriazole (HOBT), CH₂Cl₂;
(b) CH₃CO₂⁻ NH₄⁺, EtOH, under reflux;
(c) COCl₂, toluene, under reflux; or POCl₃, under reflux;
(d) hydrazine hydrate, dimethylsulphoxide (DMSO), under reflux;
(e) ethyl malonyl chloride, EtOAC at 0° C.;
(f) p-toluenesulphonic acid (pTSA), toluene, under reflux;
(g) NaH, R³Cl or R³Br, N,N-dimethylformamide (DMF);
(h) NaOH, EtOH, H₂O; (i) 1 M HCl

SCHEME 2

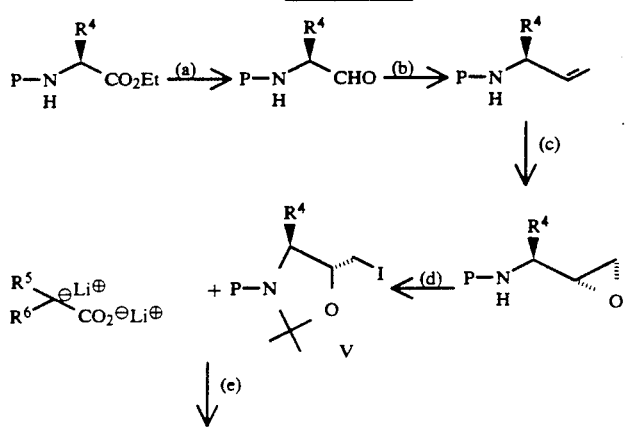

SCHEME 2

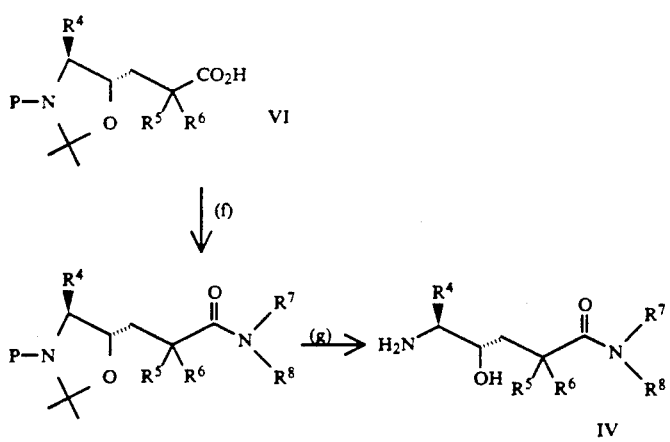

Reagents (a) Diisobutylaluminium hydride, toluene, −40° C.;
(b) $Ph_3P^+.CH_3Br^-$, potassium hexamethyldisilazide, THF, DMSO;
(c) m-Chloroperbenzoic acid;
(d) $(CH_3)_3SiCl$, NaF, $CH_3.CN$; then AcOH, NaI; then $CH_3.C(CH_3O)2.CH_3$, pTSA, $CH_2Cl_2$
(e) Hexamethylphosphorustriamide, THF;
(f) 1-Ethyl-3-(dimethylamino)propylcarbodiimide, HOBT, $ET_3N$, $R^7R^8NH$;
(g) Ammonium formate, palladium-carbon, EtOH, $H_2O$

SCHEME 3

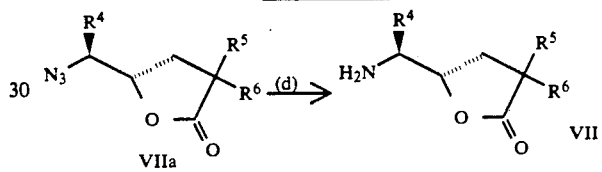

Note: P = benzyloxycarbonyl

Reagents (a) HCl, dioxane, water;
(b) Ammonium formate, palladium-carbon, EtOH;
(c) 1-Ethyl-3-(dimethylamino)propylcarbodiimide hydrochloride, HOBT, $H_2O$ and DMF
(d) Hydrogen, palladium-carbon, EtOH

CHEMICAL FORMULAE
(Description)

CHEMICAL FORMULAE
(Description)
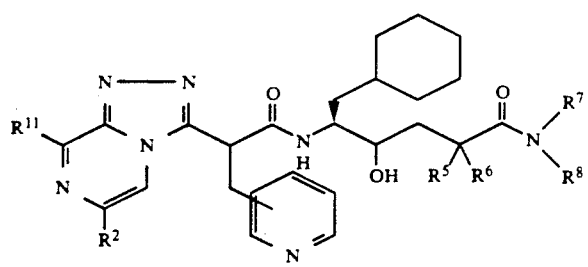
II
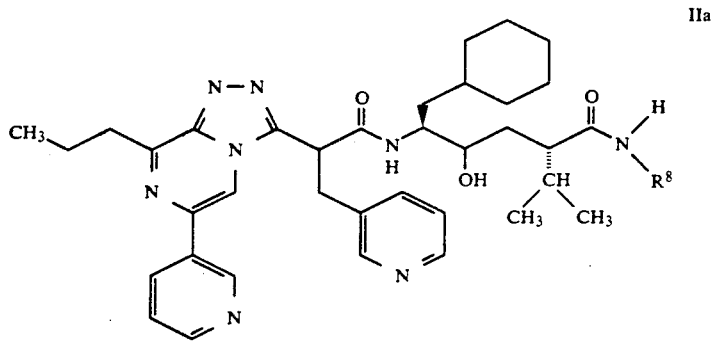
IIa
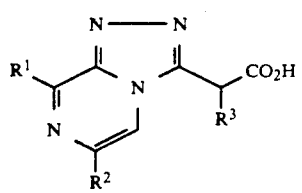
III
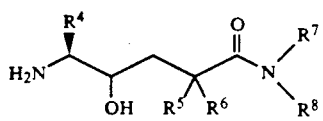
IV
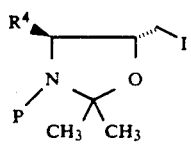
V
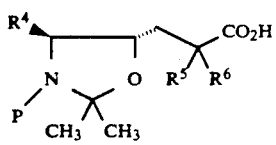
VI
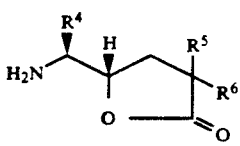
VII
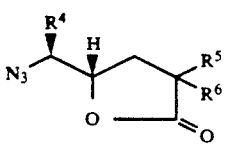
VIIa

CHEMICAL FORMULAE
(Description)

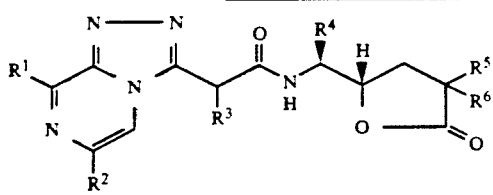

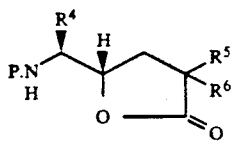

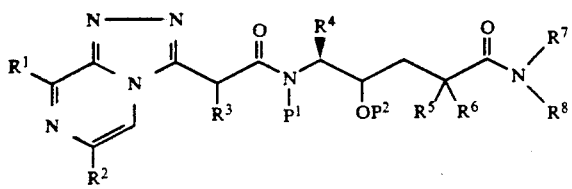

VIII

IX

X

What is claimed is:

1. A heterocyclic amide of the formula I

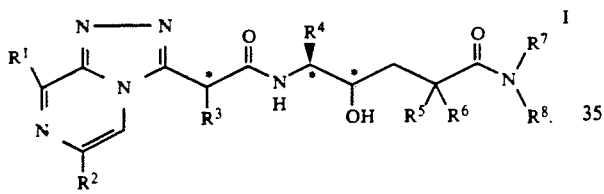

wherein $R^1$ is (1-8C)alkyl or phenyl;

$R^2$ is phenyl or pyridyl, the latter optionally bearing a (1-4C)alkyl substituent;

$R^3$ is hydrogen or a group of the formula $Q^1A^1$-in which $Q^1$ is selected from pyridyl, imidazolyl, thiazolyl and pyrazolyl, and $A^1$ is methylene or ethylene;

$R^4$ is (1-8C)alkyl or (3-8C)cycloalkyl-(1-4C)alkyl;

$R^5$ is hydrogen or (1-4C)alkyl;

$R^6$ is hydrogen, (1-6C)alkyl, (1-4C)alkoxy, hydroxy, (1-4C)alkylthio, (1-4C)alkylsulphinyl, (1-4C)alkylsulphonyl, or a group of the formula $Q^2A^2$- in which $Q^2$ is selected from (1-4C)alkoxy, (2-4C)alkenyl, phenyl and hydroxy, and $A^2$ is (1-4C)alkylene;

or $R^5$ and $R^6$ together form (2-4C)alkylene;

and wherein $R^7$ is hydrogen, (1-4C)alkyl or hydroxy(2-4C)alkyl; and $R^8$ is hydrogen, (1-4C)alkyl in which 2 or 3 carbon atoms may bear a hydroxy substituent, (1-8C)alkyl, a group of the formula $Q^3A^3$- in which $Q^3$ is selected from (1-4C)alkoxy, morpholino, thiomorpholino, piperidino, pyrrolidino, N-(1-4C)piperazinyl, pyridyl (itself optionally bearing a (1-4C)alkyl substituent) and phenyl (itself optionally bearing 1 or 2 substituents independently selected from halogeno, trifluoromethyl, cyano, (1-4C)alkyl, (1-4C)alkoxy, amino(1-4Calkyl), and $A^3$ is (1-4C)alkylene; or $R^8$ is a group of the formula $Q^4A^4$-in which $Q^4$ is selected from amino, hydroxy and N,N-di-(1-4C)alkylamino, and $A^4$ i (1-8C)alkylene;

or $R^7$ and $R^8$ together with the adjacent nitrogen complete a morpholino, thiomorpholino, piperidino, pyrrolidino or N-(1-4C)piperazinyl moiety;

and wherein a phenyl moiety of $R^1$, $R^2$ or $Q^2$, may optionally bear 1 or 2 substituents independently selected from halogeno, trifluoromethyl, cyano, (1-4C)alkyl and (1-4C)alkoxy;

or a pharmaceutically acceptable salt thereof when $R^2$, $R^3$, or $R^8$, or $R^7$ and $R^8$ contain a basic group.

2. A heterocyclic amide as claimed in claim 1 wherein $R^1$ is selected from methyl, ethyl, propyl, isopropyl, butyl, isobutyl, sec-butyl, t-butyl, pentyl, isopentyl, 1-methylbutyl, hexyl, 1-methylpentyl, 1,1-dimethylbutyl and phenyl;

R2 is selected from phenyl and 3-pyridyl, the latter optionally bearing a methyl or ethyl substituent;

$R^4$ is selected from methyl, ethyl, propyl, isopropyl, butyl, isobutyl, sec-butyl, t-butyl, pentyl, isopentyl, 1-methylbutyl, hexyl, 1-methylpentyl, 1,1-dimethylbutyl, cyclopropylmethyl, cyclopentylmethyl and cyclohexylmethyl;

$R^5$ is selected from hydrogen, methyl, ethyl, isopropyl and isobutyl;

$R^6$ is selected from hydrogen, methyl, ethyl, isopropyl, isobutyl, methoxy, ethoxy, propoxy, hydroxy, methylthio, ethylthio, methylsulphinyl, ethylsulphinyl, methylsulphonyl, ethylsulphonyl and a group of the formula $Q^2A^2$- in which $Q^2$ is selected from methoxy, ethoxy, isopropoxy, isobutoxy, vinyl, 1-propenyl, allyl, 1-butenyl, phenyl and hydroxy, and $A^2$ is selected from methylene, ethylene and trimethylene;

or $R^5$ and $R^6$ together form ethylene, propylene or tetramethylene; and wherein $R^7$ is selected from hydrogen, methyl, ethyl, isopropyl, isobutyl, 2-hydroxyethyl and 2-hydroxypropyl; and $R^8$ is selected from hydrogen, 2-hydroxy-(hydroxymethyl)ethyl, 2-hydroxy-1,1-di(hydroxymethyl)ethyl, methyl, ethyl, propyl, isopropyl, butyl, isobutyl, sec-butyl, t-butyl, pentyl, isopentyl, 1-methylbutyl, hexyl, 1-methylpentyl, 1,1-dimethylbutyl and a group of the formula $Q^3A^3$- in which $Q^3$ is selected from methoxy, ethoxy, isopropoxy, isobutoxy, morpholino, thiomorpholino, piperidino, pyrrolidino, N-methylpiperazinyl, N-ethylpiperazinyl, N-propylpiperazinyl, pyridyl (itself optionally bearing a methyl or ethyl substituent) and phenyl (itself optionally bearing 1 or 2 substituents independently selected from fluoro, chloro, bromo, trifluoromethyl, cyano, methyl, ethyl, ispropyl, butyl, methoxy, ethoxy, propoxy, isopropoxy, aminomethyl, 2-aminoethyl and 3-aminopropyl, and $A^3$ is selected from methylene, ethylene and trimethylene; or $R^8$ is a group of the formula $Q^4A^4$-in which $Q^4$ is selected from amino, hydroxy, dimethylamino and diethylamino, and $A^4$ is selected from methylene, ethylene, trimethylene and tetramethylene in any of which an individual methylene may optionally bear a methyl, ethyl, isopropyl or isobutyl substituent; or $R^7$ and $R^8$ together with the adjacent nitrogen complete a morpholino, thiomorpholino, piperidino, pyrrolidino, N-methylpiperazinyl, N-ethylpiperazinyl or N-propylpiperazinyl moiety; and wherein a phenyl moiety of $R^1$, $R^2$ or $Q^2$ may optionally bear 1 or 2 substituents independently selected from fluoro, chloro, bromo, trifluoromethyl, cyano, methyl, ethyl, isopropyl, butyl, methoxy, ethoxy, propoxy and isopropoxy;

or a pharmaceutically acceptable salt thereof when $R^2$, $R^3$ or $R^8$, or $R^7$ and $R^8$ contain a basic group.

3. A heterocyclic amide as claimed in claim 1 wherein $R^8$ is selected from methyl, ethyl, propyl, butyl, 2-hydroxy-1-(hydroxymethyl)ethyl, 2-hydroxy-1,1-di(hydroxymethyl)ethyl, methoxyethyl, ethoxyethyl, 2-(N-morpholino)ethyl, 2(N-piperazinyl)ethyl, 2-pyridylmethyl, 3-pyridylmethyl, 2-(3-pyridyl)ethyl, benzyl, chlorobenzyl, bromobenzyl, cyanobenzyl, 1-phenylethyl, 2-phenylethyl, 2-(hydroxymethyl)-3-methylbutyl, 2-(aminomethyl)-3-methylbutyl, 2-hydroxy-1,1-dimethylethyl, 2-(dimethylamino)ethyl, 2-(N-piperazinyl)ethyl, 2-hydroxyethyl and 4-hydroxybutyl; and $R^7$ is selected from hydrogen, methyl, ethyl and 2-hydroxyethyl; or $R^7$ and $R^8$ together with the adjacent nitrogen complete a morpholino, piperidino, pyrrolidino or N-methylpiperazino moiety.

4. A heterocyclic amide of the formula II

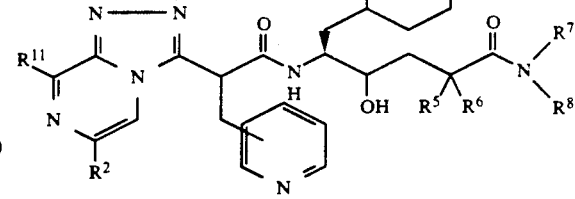

wherein $R^{11}$ is (1-6C)alkyl and $R^2$, $R^5$, $R^6$, $R^7$ and $^8$ have any of the meanings defined in claim 1; or a pharmaceutically acceptable salt thereof.

5. A heterocyclic amide of the formula II according to claim 4 wherein $R^{11}$ is propyl or isobutyl; $R^2$ is 3-pyridyl or phenyl; $R^5$ is hydrogen or methyl; $R^6$ is methyl, propyl, isopropyl, butyl, 2-methylpropyl or methoxymethyl; $R^7$ is hydrogen; and $R^8$ is methyl, butyl, methoxyethyl, 2-(dimethylamino)ethyl, 3-pyridylmethyl, 2-(N-morpholino)ethyl; or a pharmaceutically acceptable salt thereof.

6. A heterocyclic amide of the formula IIa

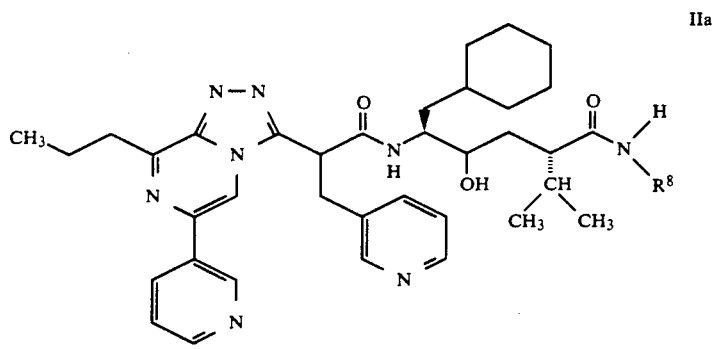

wherein $R^8$ has any of the meanings as claimed in claim 5; or a pharmaceutically acceptable salt thereof.

7. (2S,4S,5S)-N-Butyl-6-cyclohexyl-4-hydroxy-2-isopropyl-5-[(2R S)-2-(8-propyl-6-(3-pyridyl)-1,2,4-triazolo[4,3-a]pyrazin-3-yl)-3-(3-pyridyl)propionamido]hexanamide; or a pharmaceutically acceptable salt thereof.

8. A pharmaceutically acceptable salt as claimed in claim 1, 4 or 6 selected from acid-addition salts with hydrogen halides, sulphuric acid, phosphoric acid and organic acids affording physiologically acceptable anions.

9. A pharmaceutical composition for inhibiting the catalytic action of renin in a warm-blooded animal which comprises a therapeutically effective amount of a compound of the formula I, II or IIa, or a pharmaceutically acceptable salt thereof, as defined in claim 1, 4 or 6, together with a pharmaceutically acceptable diluent or carrier.

10. A method of inhibiting the catalytic action of renin in the formation of angiotensins in a warm blooded animal requiring such treatment which comprises administering to said animal a therapeutically effective amount of a compound of the formula I, II or IIa, or a pharmaceutically acceptable salt thereof, as defined in claim 1, 4, or 6.

11. A method of producing a hypotensive effect in a warm blooded animal requiring such treatment which comprises administering to said animal an effective amount of a compound of the formula I, II or IIa, or a pharmaceutically acceptable salt thereof, as defined in claim 1, 4 or 6.

12. A compound of formula VIII

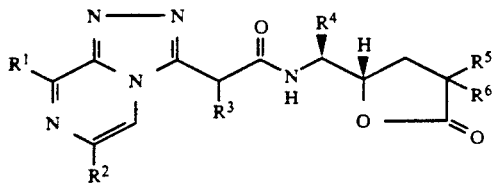

wherein

R¹ is (1-8C)alkyl or phenyl;

R² is phenyl or pyridyl, the latter optionally bearing a (1-4C)alkyl substituent;

R³ is hydrogen or a group of the formula Q¹A¹- in which Q¹ is selected from pyridyl, imidazolyl, thiazolyl and pyrazolyl, and A¹ is methylene or ethylene;

R⁴ is (1-8C)alkyl or (3-8C)cycloalkyl-(1-4C)alkyl;

R⁵ is hydrogen or (1-4C)alkyl;

R⁶ is hydrogen, (1-6C)alkyl, (1-4C)alkoxy, hydroxy, (1-4C)alkylthio, (1-4C)alkylsulphinyl, (1-4C)alkylsulphonyl, or a group of the formula Q² A²- in which Q² is selected from (1-4C)alkoxy, (2-4C)alkenyl, phenyl and hydroxy, and A² is (1-4C)alkylene;

or R⁵ and R⁶ together form (2-4C)alkylene;

and wherein a phenyl moiety of R¹, R² or Q², may optionally bear 1 or 2 substituents independently selected from halogeno, trifluoromethyl, cyano, (1-4C)alkyl and (1-4C)alkoxy;

or a pharmaceutically acceptable salt thereof when 2 or R³ contains a basic group.

* * * * *